US008840788B2

(12) United States Patent
Ohno et al.

(10) Patent No.: US 8,840,788 B2
(45) Date of Patent: Sep. 23, 2014

(54) HOLLOW FIBER MEMBRANE, METHOD FOR MANUFACTURING THE SAME, AND BLOOD PURIFICATION MODULE

(75) Inventors: Makoto Ohno, Ohtsu (JP); Isamu Yamamoto, Ohtsu (JP); Takahito Sagara, Ohtsu (JP); Kimihiro Mabuchi, Iwakuni (JP); Tohru Uenishi, Ohtsu (JP); Shinya Koyama, Ohtsu (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 352 days.

(21) Appl. No.: 13/147,721

(22) PCT Filed: Feb. 2, 2010

(86) PCT No.: PCT/JP2010/051395
§ 371 (c)(1),
(2), (4) Date: Aug. 3, 2011

(87) PCT Pub. No.: WO2010/090174
PCT Pub. Date: Aug. 12, 2010

(65) Prior Publication Data
US 2011/0290709 A1     Dec. 1, 2011

(30) Foreign Application Priority Data

Feb. 4, 2009  (JP) ................................. 2009-023252
Mar. 19, 2009 (JP) ................................. 2009-068156
Jul. 16, 2009  (JP) ................................. 2009-167376

(51) Int. Cl.
*B01D 69/08* (2006.01)
*B01D 63/02* (2006.01)
*B01D 71/68* (2006.01)
*A61M 1/16* (2006.01)

(52) U.S. Cl.
CPC .............. *B01D 69/087* (2013.01); *B01D 71/68* (2013.01); *A61M 1/1621* (2014.02); *B01D 63/02* (2013.01); *B01D 2313/04* (2013.01)
USPC ............... 210/321.8; 210/321.89; 210/500.23

(58) Field of Classification Search
USPC ................. 210/321.6, 321.79, 321.8, 321.88, 210/321.89, 500.23
See application file for complete search history.

(56) References Cited

U.S. PATENT DOCUMENTS

| | | | | | |
|---|---|---|---|---|---|
| 5,851,394 | A | * | 12/1998 | Shibata et al. | ............ 210/500.23 |
| 6,632,359 | B1 | * | 10/2003 | Uezumi et al. | ............ 210/500.23 |
| 2004/0206692 | A1 | | 10/2004 | Oishi et al. | |
| 2007/0080108 | A1 | | 4/2007 | Kuroda et al. | |

FOREIGN PATENT DOCUMENTS

| | | |
|---|---|---|
| EP | 1 129 738 A1 | 9/2001 |
| EP | 1 410 839 A1 | 4/2004 |
| EP | 1 733 783 A1 | 12/2006 |
| GB | 2 047 161 A | 11/1980 |
| JP | 3-62431 B2 | 9/1991 |
| JP | 05-049879 A | 3/1993 |
| JP | 07-185278 A | 7/1995 |
| JP | 10-108907 A | 4/1998 |
| JP | 2000-042383 A | 7/1998 |
| JP | 10-216488 A | 8/1998 |
| JP | 2002-045420 A | 2/2002 |
| JP | 2002-186667 A | 7/2002 |
| JP | 2003-033632 A | 2/2003 |
| JP | 2003-210573 A | 7/2003 |
| JP | 2003-275300 A | 9/2003 |
| JP | 2004-305561 A | 11/2004 |
| JP | 2004-305677 A | 11/2004 |
| JP | 2005-058905 A | 3/2005 |
| JP | 2006-000373 A | 1/2006 |
| JP | 2006-051094 A | 2/2006 |
| JP | 2006-288413 A | 10/2006 |
| JP | 2006-340977 A | 12/2006 |
| JP | 2007-105700 A | 4/2007 |
| WO | 2005/046763 A1 | 5/2005 |

OTHER PUBLICATIONS

Akiba et al. "Journal of the Japanese Society for Dialysis Therapy", 2008, 41(3), pp. 159-167, w/ English abstract, cited in spec.
International Search Report for PCT/JP2010/051395, mailing date of May 11, 2010.
Extended European Search Report dated Jun. 17, 2013, issued in corresponding European Patent Application No. 10738506.4 (10 pages).

* cited by examiner

*Primary Examiner* — John Kim
(74) *Attorney, Agent, or Firm* — Westerman, Hattori, Daniels & Adrian, LLP

(57) ABSTRACT

The present invention provides a hollow fiber membrane where the membrane strength and pressure resistance to pressurization from the dialysate side is ensured, the retaining rate of water permeability after the repeated pressure load from outside is high, the resistance to the pressure from outside is excellent and the assembling property into module (low leakage rate at the adhered part) is satisfactory at the same time. The present invention also provides a method for manufacturing the same, and a blood purification module.

5 Claims, 1 Drawing Sheet

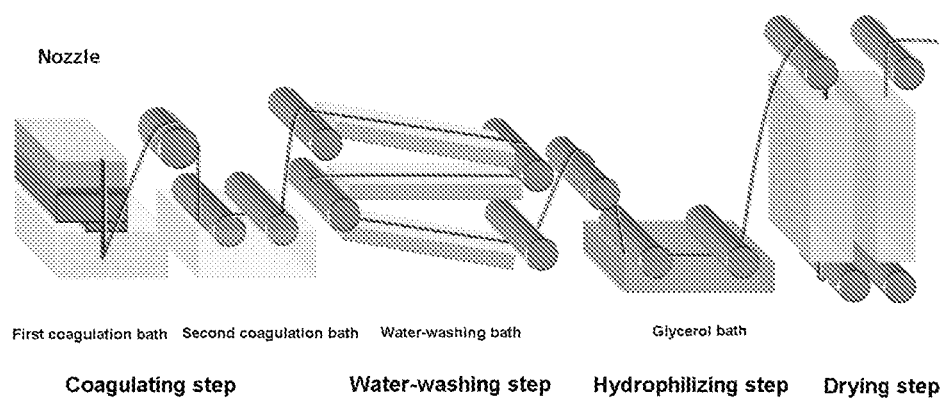

HOLLOW FIBER MEMBRANE, METHOD FOR MANUFACTURING THE SAME, AND BLOOD PURIFICATION MODULE

TECHNICAL FIELD OF THE INVENTION

The present invention relates to a hollow fiber membrane used for blood purification such as hemodialysis, hemofiltration or hemodiafiltration. More particularly, it relates to a hollow fiber membrane having both safety and high dialysis performance where, as a result of making its water permeability low, invasion of endotoxin from the dialysate into the blood can be prevented and, in spite of its low water permeability, low-molecular protein represented by β2 microglobulin (β2MG) can also be removed. It further relates to an excellent hollow fiber membrane and a blood purification module where the risk of leakage during assembling the blood purification module and during dialysis session is small since its resistance to the pressure from outside is significantly enhanced as compared with the conventional hollow fiber membrane. It furthermore relates to a hollow fiber membrane and a blood purification module where lowering of the quality due to changes in the temperature during storage and transportation is little and a predetermined property can be expressed in its clinical use since its strength and elongation are high and its heat resistance is excellent. It still further relates to a method for the manufacture of a hollow fiber membrane where the retaining rate of water permeability after the repeated pressure load from outside is high, resistance to the pressure from outside is excellent and an assembling property for module (low leakage rate at the adhered part) is satisfactory.

BACKGROUND ART

Hemodialysis has been already carried out as a maintenance therapy for the patients suffering from chronic renal insufficiency. Further, working examples of the therapy such as continuous hemofiltration, continuous hemodiafiltration or continuous hemodialysis are increasing in recent years as an acute blood purification therapy for the patients of a severely diseased state suffering from, for example, acute renal insufficiency and sepsis. As to a material of hollow fiber membrane used for such a therapy, there have been utilized a material derived from nature such as cellulose or cellulose derivatives and a synthetic polymer material such as polysulfone resin, poly(methyl methacrylate), polyacrylonitrile or ethylene-vinyl alcohol copolymer.

Hemodialysis is carried out for two to three times a week and, since it is a maintenance therapy throughout the life, although the module for the hemodialysis is important for its dialyzing property, the safety thereof is also quite important. In order to achieve the high performance of the hollow fiber membrane, the so-called water permeation heightening where the permeability of the membrane to water is enhanced is common but, as a result of making the water permeation high, there is a risk that the membrane strength lowers or particularly the pressure resistance and strength to the pressurization from the dialysate side lower whereby detachment and leakage are resulted. In addition, as a result of making the water permeation high, there are problems such as a risk where the dialysate invades into the body of a patient by a backfiltration during the dialysis and the lowering of the strength to the pressure particularly from the dialysate side as well as occurrence of the detachment of adhered part of the hollow fiber membrane and the generation of leakage.

On the basis of the recognition that the contamination of the dialysate and the lack of biocompatibility of the blood purification module are the factors for the onset of a long-term complication of the dialyzing patient with amyloidosis or the like, the Japanese Society for Dialysis Therapy proposed the standard for water quality of the dialysate and the standard for property evaluation of the blood purification modules. (See Non-Patent Document 1.)

The present applicant already filed a patent application for the membrane where the smoothness of the membrane is enhanced by subjecting to an appropriate elongation in a coagulation bath so as to give a membrane being excellent in safety and efficiency-retaining ability where the water permeating efficiency is 1 to 30 mL/(m²·hr·mmHg) (See Patent Document 1). In this technique, the inner structure of the membrane is made into a uniform fine structure and the surface smoothness is enhanced whereby elution of hydrophilic polymer is suppressed and efficiency-retaining rate during contacting the blood is enhanced. However, considerations in the high efficiency of the type II or more with low water permeability and also in the resistance to the pressure from the dialysate side are not sufficient.

Now, the functional classification of the dialyzer will be simply summarized as follows. (Clearance is the value calculated on the basis of 1.5 m².)

[Classification of Hollow Fiber Type and Laminated Layer Type (Keel Type)]

Type I: Its ultrafiltration rate is not less than 3.0 ml/mmHg/hr while its urea clearance is not less than 125 ml/min and it does not correspond to II to V.

Type II: Its ultrafiltration rate is not less than 3.0 ml/mmHg/hr, its urea clearance is not less than 150 ml/min, and its β2MG clearance is not less than 10 ml/min and is less than 30 ml/min.

Type III: Its ultrafiltration rate is not less than 3.0 ml/mmHg/hr, its urea clearance is not less than 150 ml/min, and its β2MG clearance is not less than 30 ml/min and is less than 50 ml/min.

Type IV: Its ultrafiltration rate is not less than 3.0 ml/mmHg/hr, its urea clearance is not less than 150 ml/min, and its β2MG clearance is not less than 50 ml/min and is less than 70 ml/min.

Type V: Its ultrafiltration rate is not less than 3.0 ml/mmHg/hr, its urea clearance is not less than 150 ml/min, and its β2MG clearance is not less than 70 ml/min.

In the Patent Document 2, there is disclosed a hollow fiber type blood purification module containing hollow fiber membranes comprising hydrophobic polymer and hydrophilic polymer where elution of the hydrophilic polymer is not more than 20 mg per m² and a retaining rate of the water permeability during perfusion using bovine blood is excellent. According to this document, it is mentioned that a non-coagulating inner liquid is used and the coagulation bath temperature is made low whereby coagulation of a spinning dope of polyether sulfone is made mild whereupon the membrane structure can be made uniform and smooth. It is also mentioned that the fine structure is made optimum by giving an appropriate elongation in a coagulation bath. However, the hollow fiber membrane mentioned in this document is such a thing where its coagulating speed is controlled so that elution of the hydrophilic polymer is suppressed and membrane structure is made smooth and, further, deformation of pores is suppressed so that the efficiency-retaining ability during contacting the blood is enhanced. Thus, although it is a low water-permeating and well usable blood purification module in which contamination from the dialysate during dialysis is suppressed, it is not in such a membrane structure having excellent removing property of the low-molecular protein.

On the other hand, the Patent Document 3 discloses a hollow fiber type blood purification module for medical use having a high water permeating ability used for the treatment of chronic renal insufficiency where safety and module assembling property are excellent. More specifically, it is mentioned that membrane thickness of polysulfone hollow fiber membrane is not more than 60 μm, breaking strength of a single fiber is not more than 50 g, yield strength is not more than 30 g, and crimps where wavelength is not less than 10 mm and amplitude is not less than 0.2 mm are given to the hollow fiber membrane; that the rate of the modified hollow fiber membrane consisting of all of flat fiber, abnormally shaped fiber and clogged fiber contained in the adhered terminal surface during assembling the hollow fiber membrane into a blood purification module is not more than 0.5% of the total numbers of the cross section of the hollow fiber membrane; and that the urea clearance measured by using a blood purification module having 1.5 m$^2$ membrane area based on the inner diameter of the hollow fiber membrane is not less than 160 mL/min. However, the hollow fiber membrane mentioned in said document is intended to be a highly efficient blood purification module by making the water permeability high and, for enhancing the strength of the hollow fiber membrane, the structure is made asymmetric and, further, the membrane thickness is made large.

The Patent Document 4 discloses a hydrophilized selective permeating membrane comprising hydrophobic polymer and hydrophilic polymer wherein the membrane structure is made into a uniform fine structure so that elution can be suppressed even if the hydrophilic polymer is not subjected to a cross-linking treatment. There is mentioned that, according to this technique, permeability of low-molecular solutes (urea where the molecular weight is 60; inulin where the molecular weight is 5200) is high in spite of the fact the membrane has low water permeability and that the UV absorption thereof measured according to the standards for the approval of dialysis-type artificial kidney devices is 0.00. However, the invention mentioned in this publication relates to a hydrophilized selective permeable membrane of the conventional low water permeation type and, in this membrane, removal of low-molecular proteins such as β2MG (where the molecular weight is 11600) is difficult.

The Patent Document 5 discloses a hollow fiber membrane where high resistance to chemicals and physical strength are available and, even when a treatment with chemicals and a backwashing for the regenerating treatment are conducted, the hydrophilic polymer is not flown out from the membrane and the separating property is not deteriorated. According to the description of this document, the outcome is that, in case a spinning dope wherein the concentration (viscosity) of the polymers therein is made within a specific range is used, the entire membrane is made into a tight and uniform structure and the hydrophilic polymer is locked in that structure whereupon the above-mentioned action and effect are achieved. However, in the hollow fiber membrane mentioned in this document, its membrane thickness is made large so as to enhance the fiber strength for such a purpose that not the pressure resistance during dialysis but the resistance to chemical treatment and also to backwashing is to be enhanced.

The Patent Document 6 discloses a hollow fiber membrane having high water permeability and large pore size for the plasma separation where the membrane comprises a copolymer of ethylene vinyl alcohol. This hollow fiber membrane has the thickness of 15 to 17 μm and the breakage strength of 2.1 to 4.1 kg/cm$^2$ (0.2 to 0.4 MPa) when a blood purification module is formed from this hollow fiber membrane and the blood outlet of the module is sealed under such a state that the module is dipped in water of 37° C., then pressure of air is gradually applied from the blood inlet and then the hollow fiber membrane is broken.

PRIOR ART DOCUMENTS

Patent Documents

Patent Document 1: Japanese Patent Application Laid-Open (JP-A) No. 2004-305561
Patent Document 2: Japanese Patent Application Laid-Open (JP-A) No. 2004-305677
Patent Document 3: Japanese Patent Application Laid-Open (JP-A) No. 2006-000373
Patent Document 4: Japanese Patent Application Laid-Open (JP-A) No. 2000-042383
Patent Document 5: Japanese Patent Application Laid-Open (JP-A) No. 216488/98
Patent Document 6: Japanese Patent Application Laid-Open (JP-A) No. 185278/95

Non-Patent Documents

Non-Patent Document 1: Akiba et al., Journal of the Japanese Society for Dialysis Therapy, 2008, 41 (3), pp. 159-167

DISCLOSURE OF THE INVENTION

Problem that the Invention is to Solve

Development in the past for making the membrane highly efficient or for the enhancement of the property for removal of low-molecular protein such as the so-called β2 microglobulin has been conducted in such a manner that the water permeability is made high where pore size and effective poring rate are enhanced. Accordingly, water permeability of the membrane is enhanced as the efficiency becomes high but a risk where pyrogen such as endotoxin in the dialysate passes through the permeable membrane to mix into the blood during the dialysis increases to such an extent. Further, as a result of enhancement of pore size and poring rate of the membrane due to making the water permeability high, strength of the membrane lowers. Particularly, the lowering of the strength and resistance to the pressure due to the pressurization from the dialysate side not only increases the contamination risk of pyrogen but also results in a risk of leakage of the blood during the dialysis by way of leakage and detachment of adhered part of the hollow fiber. There has been also a means where the membrane thickness is made large as a method for enhancing the strength of the hollow fiber membrane but there happens a phenomenon that a lot of an agent for retaining the pore size adheres to the vacant pores of the membrane or to the membrane surface whereby the agent for retaining the pore size floats out onto the surface acting as an adhesive among the fibers and, as a result, the loosening property of the fiber is deteriorated whereupon the assembling yield of the module is deteriorated.

An object of the present invention is to solve the problems in the above-mentioned prior art and is to provide a hollow fiber membrane which is safe and easily usable and has high efficiency and a method for manufacturing the same as well as a blood purification module wherein the high efficiency of type II or higher according to the functional classification stipulated by the Japanese Society for Dialysis Therapy is available while the water permeability at 37° C. is as low as 1 to 20 mL/(m²·hr·mmHg), a risk of the so-called backfiltration where the dialysate invades into the body via a permeable membrane during the dialysis treatment due to the low water permeability is suppressed to low, pressure resistance to pressurization from the dialysate side is ensured and, further, the safety where detachment and leakage hardly happen and the efficiency expressing property are satisfied at the same time.

Another object of the present invention is to provide a hollow fiber membrane in which the hydrophilic polymer is hardly eluted, the efficiency-retaining ability during contacting the blood is excellent, an assembling property for module is excellent and a long-term preservation is also possible or, in other words, to provide a hollow fiber membrane which satisfies blood compatibility, safety, efficiency-retaining ability, economy and long-term preservability at the same time.

Means for Solving the Problem

The present inventors have conducted an intensive investigation for solving the above problems and, as a result, they have achieved the present invention. Thus, the hollow fiber membrane and a method for manufacturing the same as well as a blood purification module of the present invention are as follows.

(1) A hollow fiber membrane which is characterized in that, although its water permeability at 37° C. is as low as 1 to 20 mL/(m²·hr·mmHg), it has such a high dialysis performance that the clearance of β2 microglobulin in a blood purification module having 1.5 m² membrane area is not less than 10 mL/min, it has such a stability that the pressure resistance from the dialysate side is not less than 0.1 MPa and it substantially causes no backfiltration.

(2) The hollow fiber membrane according to (1), wherein the hollow fiber membrane is formed from a hydrophobic polymer or from a hydrophobic polymer and a hydrophilic polymer.

(3) A blood purification module, characterized in that, a plurality of the hollow fiber membranes according to the above (1) or (2) are bundled and received in a case, the end of said membrane and the end of the case are fixed with each other using an adhesive resin and then both ends are cut to open the hollow area.

(4) The blood purification module according to (3), wherein neither detachment nor leakage of the hollow fiber membrane happens even when the pressure of 0.2 MPa is applied from the dialysate side.

(5) A hollow fiber membrane, characterized in that, the membrane thickness is 10 to 50 μm, the membrane structure is in a substantially uniform structure, the yield strength is 35 g/filament to 70 g/filament and the yield elongation is from 3%/filament to 10%/filament.

(6) The hollow fiber membrane according to (5), wherein the breakage strength is not less than 40 g/filament and the breakage elongation is not less than 50%/filament.

(7) The hollow fiber membrane according to (5) or (6), wherein the roughness (Ra) of the inner surface of the hollow fiber membrane measured by an atomic force microscope (AFM) is less than 10 nm.

(8) The hollow fiber membrane according to any of (5) to (7), wherein the length of the hollow fiber membrane after a hollow fiber membrane in 20.0 cm length is tightly sealed in an aluminum bag and heated at 80° C. for 20 hours is not less than 19.0 cm.

(9) The hollow fiber membrane according to any of (5) to (8), wherein it comprises a polysulfone-based polymer and polyvinylpyrrolidone.

(10) A blood purification module where a hollow fiber membrane is included therein, characterized in that, water permeability for pure water at 37° C. is 1 to 30 mL/(m²·hr·mmHg) and the urea clearance measured under the condition where the flow rate of the test solution of the blood side is 200 mL/min and the flow rate of the test solution of the dialysate side is 500 mL/min is not less than 120 mL/(min·m²).

(11) The blood purification module according to (10), wherein the urea clearance after the blood purification module is tightly sealed in an aluminum bag and heated at 80° C. for 20 hours has a retaining rate of not less than 80% for the urea clearance before the heating treatment.

(12) A method for the manufacture of a hollow fiber membrane which comprises the steps where a spinning dope in which a polymer is dissolved is discharged into a coagulation bath from a tube-in-orifice nozzle via a running passage in the air, washed with water in a water-washing bath, made hydrophilic and dried, characterized in that, the spinning dope is elongated in a coagulation bath to an extent of 10 to 65%, then elongated in a water-washing bath to an extent of 2 to 10% and dried at 20 to 50° C. in the drying step substantially without elongation.

(13) The hollow fiber membrane obtained by the manufacturing method according to (12), wherein the retaining rate of the water permeability after the repeated loading of pressure from outside is not less than 80%, a priming volume of not less than 50% is retained by the pressure of 0.1 MPa from the dialysate side, neither leakage nor detachment damage of the hollow fiber membrane happens by the pressure of 0.2 MPa from the dialysate side and the leakage rate at the adhered part during assembling the module is not more than 5%.

(14) The hollow fiber membrane according to (13), wherein the water permeability is 1 to 25 mL/(m²·hr·mmHg) and the yield strength is not less than 33 g/filament.

Advantages of the Invention

In spite of the fact that the water permeability at 37° C. is as low as 1 to 20 mL/(m²·hr·mmHg), it has been noted that the hollow fiber membrane and the blood purification module of the present invention have high β2 microglobulin clearance in a blood purification module having 1.5 m² membrane area of not less than 10 mL/min (efficiency of type II or higher in accordance with the functional classification stipulated by the Japanese Society for Dialysis Therapy). In addition, due to the low water permeability and the high strength, it has been noted that resistance to pressure is still available even when the pressure of 0.1 MPa is applied to the dialysate side and that neither detachment nor leakage of the hollow fiber membrane happens even when the pressure of 0.2 MPa is applied for 4 hours. It has been therefore noted that a risk where the dialysate invades into a patients during the dialysis treatment or a risk of the so-called backfiltration does not happen.

Moreover, in accordance with the present invention, it is now possible to provide a hollow fiber membrane in which the hydrophilic polymer is hardly eluted from the hollow fiber membrane, the efficiency-retaining ability during contacting the blood is excellent, an assembling property for module is excellent and a long-term preservation is also possible or, in other words, to provide a hollow fiber membrane which satisfies blood compatibility, safety, efficiency-retaining ability, economy and long-term preservability at the same time.

Still further, in the hollow fiber membrane obtained by the manufacturing method of the present invention, the retaining rate of the water permeability after the repeated loading of the pressure from outside is not less than 80%, a priming volume of not less than 50% is retained by the pressure of 0.1 MPa from the dialysate side, neither leakage nor detachment damage of the hollow fiber membrane happens by the pressure of 0.2 MPa from the dialysate side and the bad adhesion rate during assembling the module is low. Accordingly, the hollow fiber membrane of the present invention has no problem in terms of safety due to lowering of the membrane strength as a result of making the water permeability high and also has very high productivity.

BRIEF DESCRIPTION OF THE FIGURE

FIG. 1 is a chart showing the outline of the steps for the manufacture of the hollow fiber membrane of the present invention.

BEST MODE FOR CARRYING OUT THE INVENTION

With regard to a method for manufacturing the membrane, there are several methods such as, for example, a method where a plasticizer is added to polyolefin and melted and the plasticizer is removed by means of extraction to form fine pores and a method where stack lamella of polyolefin is elongated to cleave whereupon fine pores are formed. However, the mainstream method is that where solvent or non-solvent is added to the polymer to dissolve and, after that, porous membrane is prepared by means of a micro phase separation. It can be said that the separation membrane for the hemodialysis is substantially prepared by a micro phase separation method. In the phase separation process in the actual membrane production, a polymer solution is discharged from a nozzle and then subjected to a coagulating process. The present inventors have conducted intensive investigations therefor and found that the coagulating process is a shrinking process due to gelling and that the membrane shrinks when the hollow fiber membrane which still contains a lot of solvent is dipped in water from the coagulation bath.

Since the conventional process for the manufacture of membrane is a shrinking process due to gelling, unevenness due to the shrinking is inevitably generated in the separated structure part regardless of whether the membrane structure is uniform or asymmetric and it is likely that the unevenness acts as a resistance at the stage of membrane separation causing a decrease in the efficiency. Therefore, for making the efficiency of the membrane high, it is absolutely necessary that the pore size and the poring rate of the membrane are to be made large against the substantial membrane resistance due to the shrunk unevenness whereby there is a necessity of enhancing the water permeability by all means.

Moreover, in order to enhance the efficiency for the removal of the waste products in the hemodialysis such as urea, it is necessary that blood and dialysate are to be flown oppositely or, in other words, in a counter current manner and, in a blood purification module where such a flow is adopted, the outlet side for the blood is positioned at the inlet side for the dialysate. In the meanwhile, if a flow exists, the pressure drop is resulted necessarily. Accordingly, in the usual hemodialysis, the pressure at the inlet side for the dialysate is higher than the pressure at the outlet side for the blood whereupon the backfiltration in which the dialysate comes into the blood may happen. Although the degree of the backfiltration may dependent upon the form of the blood purification module and the pressure drop, the backfiltration is apparently significant in a membrane where the water permeability is enhanced.

As a result of the intensive investigations, the present inventors have found that the degree of the backfiltration can be stipulated by viscosity of blood, flow rates of blood and dialysate, filled rate and length of blood purification module, water permeability of pure water and water permeability in blood. To be more specific, it can be approximately expressed that backfiltration speed) (mL/min)=(water permeability in blood)(mL/(m$^2$·hr·mmHg))×(membrane area)(m$^2$)×([pressure drop at the blood side]+[pressure drop at the dialysate side])(mmHg)/(1+√[(water permeability in the blood)/(water permeability of pure water at 37° C.)])/(1+√[(water permeability in the blood)/(water permeability of pure water at 37° C.)])/2. Incidentally, in the non-Patent Document 1, the backfiltration is stipulated as the inner filtration flow rate (QF) and it cites a simple estimating method by Mineshima, et al. as the citation 26. According to that, it is expressed that (backfiltration speed)(mL/min)=(water permeability in the blood)(mL/(m$^2$·hr·mmHg))×(membrane area)(m$^2$)×([pressure at the inlet side for the blood]−[pressure at the outlet side for the dialysate]−[colloid osmotic pressure π])(mmHg)/4. Since the backfiltration is such a thing where those plural parameters are combined, the present inventors carried out the dialysis in each of the forms of the blood purification module and under each of the conditions and they intensively investigated under what condition the backfiltration is stipulated. In the meanwhile, the fact whether the backfiltration happens in the actual dialysis was directly judged in such a manner that the pressure at the outlet of the blood purification module is measured to be positive or negative upon considering the colloid osmotic pressure as will be mentioned later. As a result, it has been found that, in the usual form and the usual blood purification module, the fact whether the backfiltration happens in the actual dialysis can be judged by way of the value of water permeability of pure water at 37° C. instead of the water permeability in the blood where the actual measurement is difficult and that, when the water permeability of pure water at 37° C. is as low as not more than 20 mL/(m$^2$·hr·mmHg), the influence by the backfiltration can be substantially neglected under the usual dialysis condition. The expression reading "can be substantially neglected" used here means that, in the usual dialysis, water in about two to three liters accumulated in the body is removed within a dialyzing time for about four hours whereby it is less than the water removing speed of 8.3 mL/min (=2000 mL÷240 minutes) whereby that can be neglected. When the water permeability is less than 1 mL/(m$^2$·hr·mmHg), achievement of even the minimum dialyzing efficiency is difficult whereby the water permeability is more preferred to be not less than 5 mL/(m$^2$·hr·mmHg) and further preferred to be not less than 10 mL/(m$^2$·hr·mmHg).

It is preferred in the present invention that, although the water permeability of pure water at 37° C. is as low as 1 to 20 mL/(m$^2$·hr·mmHg), there is available such a high dialysis performance that the β2 microglobulin clearance in a blood purification module having a membrane area of 1.5 m$^2$ based on the inner diameter of the hollow fiber membrane is not less than 10 mL/min. Although the detailed reason has not been clarified yet whether it is due to the device in the manufacturing condition for the hollow fiber membrane as will be mentioned later, it is presumed that, in the present invention, some changes happen in the fine structure and the pore structure of the membrane, the balance between hydrophilicity and hydrophobicity of the hollow fiber membrane, the interaction between the membrane and the protein, etc. With regard to the β2 microglobulin clearance in the blood purification therapy, it is preferred to be high. More preferably, it is not less than 12 mL/min, and further preferably, it is not less than 14 mL/min.

The present inventors have further paid their attention to the contamination from the dialysate as a problem in the actual dialysis. Contamination due to the low strength to the pressure from inside of the hollow fiber membrane as shown in the Patent Documents 3 and 6 or the so-called burst pressure or rupture damage is perceived as blood leakage by a hemodispedesis sensor during dialysis and, at that time, the dialysis therapy is stopped. The present inventors have found that the problem to which more attention is to be paid is the occurrence of contamination from the dialysate by damage or detachment of the adhered part caused by collapse due to low resistance of the hollow fiber membrane to the pressure from outside and that it is inevitable for a safe dialysis to enhance the resistance of the hollow fiber membrane to the pressure from outside.

The first condition for the resistance of the hollow fiber membrane to the pressure from outside is the resistance to the damage generated by the collapse of the hollow fiber membrane due to the pressure from outside. With regard to this resistance, it is demanded that, even when the pressure of 0.1 MPa is applied for ten minutes from the outside of the hollow fiber membrane and from the dialysate side of the blood purification module, the hollow fiber membrane is not completely collapsed but the priming volume is retained to an extent of 50% or more as compared with the case where no pressure is applied. In the actual dialysis, it is hardly presumed that the pressure of as high as 0.1 MPa is applied from outside. However, the reason why the pressure of 0.1 MPa is set is that the flow rate of the dialysate is as high as about 500 mL/min and, if abnormality such as that the outlet is temporarily clogged due to some reasons happens, 0.1 MPa can be predicted as the value corresponding to a pressure variation caused thereby.

The second condition for the resistance of the hollow fiber membrane to the pressure from outside is that the collapsed hollow fiber membrane is not detached or leaked at the adhered terminal. To be more specific, it is demanded that, even when the pressure of 0.2 MPa from the dialysate side is applied for 30 minutes, the hollow fiber membrane is not leaked or the adhered part of the hollow fiber membrane is not detached. The reason why the pressure of 0.2 MPa is set corresponds to the fact that the pressure of water or tap water supplied to the dialysis device is near 0.2 MPa when it is closed and it also corresponds to the fact that, when the re-use is conducted for example, the tap water pressure applied as the pressure from outside is about 0.2 MPa. The reason why the time is 30 minutes is that it can be said the upper limit during washing with the pressure from outside.

The third condition for the resistance of the hollow fiber membrane to the pressure from outside is that, even by the repeated pressurization from outside, the membrane does not become dense and the retention of the initial water permeability is high. To be more specific, even when the pressure of 0.2 MPa is repeatedly applied intermittently, the hollow fiber membrane does not become dense and there is almost no lowering in the initial water permeability or, in other words, retention of the water permeability after the repeated application of the pressure from outside is not less than 80%, preferably not less than 85%, and more preferably not less than 90% of the initial water permeability. The reason why the term reading "repeated application of the pressure from outside" is used is that it corresponds to the case where application of the pressure from outside is repeated for about 30 times in such a case where, for example, the re-use is done.

It is not easy to achieve such a characteristic property to the pressure from outside by the sole use of a hydrophilic polymer. Therefore, it is necessary that the hollow fiber membrane of the present invention is formed from hydrophobic polymer or from hydrophobic and hydrophilic polymers.

In order to achieve the resistance to the pressure from outside, the hollow fiber membrane of the present invention has such structural characteristics that there is no structural unevenness in the separating part of the hollow fiber membrane, that there is no deficiency such as a released layer in the thick part of the hollow fiber membrane and that it has no finger-like structure but is substantially in a continuous structure. The expression reading "substantially in a continuous structure" used herein means that, when the cross section of the membrane is observed under an electron microscope, no structural non-homogeneity can be confirmed by naked eye from a membrane surface to another membrane surface or that there is no substantial change in the structure and, in the porous layer other than the so-called skin layer, no structural non-homogeneity can be confirmed by naked eye.

On the other hand, when the hollow fiber membrane is assembled into a module, it is important that a sealing agent and an adhesive agent can easily impregnate among the hollow fiber membranes. In order to achieve the coming-loose property as such, an important requirement is to ensure the appropriate gaps among the hollow fiber membranes and another important requirement is to reduce the adhesion inhibitor between the hollow fiber membrane surface and the sealing agent. In the present invention, for a purpose of ensuring the appropriate gaps among the hollow fiber membranes, there are carried out the enhancement of the yield strength which is a yardstick for the toughness of the fiber so that the fibers are surely made loose and also the optimization of the adhered state of the retaining agent for pore sizes which works as an adhesive among the fibers if said agent becomes excessive.

In assembling the blood purification module, it improves the alignment of the hollow fiber membranes when the fiber bundle is adjusted together with applying a predetermined load so as to give the aligning property of the hollow fiber membrane bundle. On the other hand, if rigidity becomes too high, disadvantages such as that the hollow fiber membrane bundle is apt to be broken during inserting into a module case are apt to happen. Further, if the yield strength is too low, fragile hollow fiber membrane is resulted and, when it is lifted up to move, for example, in an assembling step, disadvantages such as that the hollow fiber membrane is cut are apt to happen. On the other hand, in the too much elongated hollow fiber membrane, its dimensional stability becomes poor and disadvantages such as that the assembling yield of the module is not enhanced possibly happen. In view of the above, the yield strength of the hollow fiber membrane of the present invention is preferred to be 30 g to 80 g per single fiber. It is more preferred to be 35 g to 70 g, and further preferred to be 40 g to 60 g. Further, its yield elongation per single fiber is preferred to be 3% to 10%. It is more preferred to be 3.5% to 8%, and further preferred to be 4% to 6%.

Furthermore, in the present invention, the breakage strength and the breakage elongation per single fiber of the hollow fiber membrane are preferred to be not less than 40% and not less than 50%, respectively. When the breakage strength is too low, no good workability may be available in the steps for the manufacture of the hollow fiber membrane and for making into a module while, when it is too high, the entire hollow fiber membrane becomes tight whereby there is a possibility that the expected properties cannot be achieved. Accordingly, the breakage strength of the hollow fiber membrane per single fiber is more preferred to be 45 g to 80 g, and it is further preferred to be 50 g to 75 g. Further, the breakage elongation of the hollow fiber membrane per single fiber is preferably not less than 50%. It is more preferably not less than 55% and further preferably not less than 60%. When the breakage elongation is low, there is a high possibility of fracture of the hollow fiber membrane due to physical shock and temperature change applied to the hollow fiber membrane by sterilization, transport, etc. during or after assembling the blood purification module. Although it is likely that there will be no particular problem if the breakage elongation per single fiber is too high, the upper limit of the breakage elongation is more preferred to be not more than 120%, and further preferred to be not more than 110%.

It is then preferred that, after the yield strength of the hollow fiber membrane is ensured, a hydrophilizing agent is well adhered to the pores of the hollow fiber membrane neither excessively nor deficiently and, together with suppressing the shrink of the hollow fiber membrane, enhancement of the yield of assembling the blood purification module and achievement of the property are conducted. Actually however, even when an excessive hydrophilizing agent adhered to the outer surface of the hollow fiber membrane is detached by means of scraping for example, shrinking of the hollow fiber membrane is resulted if shrinking treatment is applied by excessive drying heat or mechanical pulling is applied by elongation in the drying step thereafter whereupon the hydrophilizing agent is floated on the surface of the hollow fiber membrane or deficiency is generated in the membrane. When the hydrophilizing agent is floated on the surface of the membrane, the adhesion in assembling the module thereafter may be disturbed. Therefore, in the present invention, optimization of the adhered state of the hydrophilizing agent is carried out by means of the temperature control in the drying step.

The upper limit of the amount of the hydrophilizing agent to be impregnated in the pores of the hollow fiber membrane is preferred to be made 80% to 98% of the porosity of the hollow fiber membrane. As a result of adjustment of the above-mentioned strength/elongation of the hollow fiber membrane and amount of the hydrophilizing agent, it is now possible that the length of the hollow fiber membrane after applying the heat of 80° C. for 20 hours to the hollow fiber membrane of 20.0 cm length is kept not shorter than 19.0 cm. It is more preferred to be kept not shorter than 19.3 cm and further preferred to be kept not shorter than 19.5 cm.

On the other hand, when a water removing controller of the hemodialysis device is not used as for the patient in the initial stage of introduction but removal of water in relatively small amount is conducted in the hemodialysis treatment, it is necessary that low-molecular substances such as urea which are the causes for the disease is efficiently removed together with controlling the water permeability of the membrane low. Various means are carried out for a purpose of preventing the drift for an efficient removal of the low-molecular substances. Thus, the drift can be prevented by such means, for example, that a fin is formed on the outer circumference of the hollow fiber membrane, the filling density of the hollow fiber membrane in the blood purification module is enhanced or a physical crimp is applied to such a hollow fiber membrane which is called a Moiré structure. When a fin is installed, the shape of a nozzle becomes complicated and the control therefor is very troublesome. When the filling rate of the hollow fiber membrane in the blood purification module is enhanced, there is a possibility that the disadvantage such as the sealing agent is hardly filled therein during assembling the blood purification module happens.

Now, in the present invention, the problem as such is solved by applying the physical crimp to the hollow fiber membrane. To be more specific, it is preferred that ten or more crimps having not less than 100 µm amplitude are applied per 20 cm length of the hollow fiber membrane and, for a purpose of achieving the assembling and the compactness of the blood purification module, not less than 125 µm amplitude and not less than 13 crimps are more preferred, and not less than 150 µm amplitude and not less than 15 crimps are further preferred. Although there will be no particular problem when the crimp amplitude is too big and crimp numbers are too many, the amplitude of not more than 300 µm and the numbers of not more than 30 are appropriate as the actual mode of the crimp. When the drift is suppressed by applying the crimps as such, the urea clearance of not less than 163 mL/(min·m$^2$) can be achieved and that of even not less than 165 mL/(min·m$^2$) can also be achieved.

As to a specific means for preparing such a hollow fiber membrane, there is a method for manufacturing a membrane by means of a micro phase separation. Examples of the material for constituting the membrane include a hydrophobic polymer such as polysulfone (PSf), polyether sulfone (PES), poly(methyl methacrylate), cellulose triacetate (CTA) or cellulose diacetate (CA) and combination of said hydrophobic polymer with a hydrophilic polymer such as polyvinylpyrrolidone (PVP).

In the present invention, the polysulfone-based polymer such as PSf or PES is preferred because of its excellent biocompatibility and its ability of high removing property for the substances related to uremia and PES is particularly preferred. The polysulfone-based polymer used here may contain a functional group and substituent such as alkyl group and the hydrogen atom in its hydrocarbon skeleton may be substituted with other atom such as halogen or substituent. Incidentally, it may be used either solely or jointly by mixing two or more thereof.

Since the polysulfone-based polymer has relatively strong hydrophobicity, it tends to adsorb a plasma protein therewith when contacted the blood. Therefore, when the hollow fiber membrane is manufactured using the polysulfone-based polymer, it is usual that a hydrophilic polymer is added so that the hydrophilicity is given to enhance the compatibility to the blood. That is, since the material having a strong hydrophobicity is apt to adsorb the plasma protein, its membrane property lowers with elapse of time being affected by the plasma protein adsorbed on the surface when it is used by contacting the blood for long time. Since adsorption of the plasma protein is reduced by giving the hydrophilicity, addition of the hydrophilic polymer is effective not only for enhancing the compatibility to the blood but also for achieving the stable solute-removing property as the membrane.

The hydrophilic polymer in the present invention includes polyethylene glycol, polyvinyl alcohol, polyvinylpyrrolidone (PVP), carboxymethyl cellulose, polypropylene glycol, glycerol, starch and derivatives thereof. The use of PVP is a preferred embodiment in view of safety and economy. With regard to the molecular weight of PVP, that where the weight-average molecular weight is 10,000 to 1,500,000 may be used. To be more specific, it is preferred to use that where the molecular weight is 9,000 (K17), 45,000 (K30), 450,000 (K60), 900,000 (K80), or 1,200,000 (K90) which are commercially available from BASF. In order to achieve the aimed use, characteristic and structure, each of those hydrophilic polymers may be used solely or it is also possible to use the same two types of hydrophilic polymers having different molecular weights or an appropriate combination of two or more hydrophilic polymers of different types.

Incidentally, there is a possibility that PVP is eluted during contacting the blood when used for the blood purification and, in some cases, the possibility of resulting in an anaphylactic symptom in a patient due to the eluted PVP cannot be denied.

Although PVP is effective for making the membrane highly efficient, there is a possibility of inducing such a side effect and, therefore, its eluting amount is preferred to be as low as possible. To be more specific, it is preferred that the extracted amount of the hydrophilic polymer when the hollow fiber membrane is extracted with a 40% aqueous solution of ethanol is not more than 10 mg/m$^2$ (membrane area on the basis of the inner diameter), more preferably not more than 7 mg/m$^2$ (membrane area on the basis of the inner diameter), and further preferably it is not more than 5 mg/m$^2$ (membrane area on the basis of the inner diameter).

That which contributes in the blood compatibility and the stability of the property is believed to be mostly the hydrophilic polymer on the surface of the hollow fiber membrane. In the hollow fiber membrane of the present invention, the amount of the hydrophilic polymer on the inner surface is preferred to be 5 to 50% by weight, more preferred to be 10 to 40% by weight and further preferred to be 15 to 40% by weight. There is a possibility of resulting in an excessive adsorption of the blood components when the amount of the hydrophilic polymer is lower or higher than that. In addition, when the amount of the hydrophilic polymer is higher than that, there is a possibility that much hydrophilic polymer is eluted by contacting the blood and that may cause a problem in view of safety.

Examples of the solvent which dissolves spinning dope, hydrophobic polymer or hydrophobic and hydrophilic polymers for micro phase separation include an aprotic polar solvent such as dimethyl acetamide (DMAc), dimethyl sulfoxide (DMSO) and N-methyl-2-pyrrolidone (NMP). Among them, DMAc or NMP is preferred. Examples of the non-solvent to be added to spinning dope used for the manufacture of hollow fiber membrane include a glycol such as ethylene glycol, diethylene glycol, triethylene glycol (TEG) or polyethylene glycol and water.

Now the steps for the manufacture of the hollow fiber membrane of the present invention will be illustrated by referring to FIG. 1. Firstly, a spinning dope dissolved in a nitrogen atmosphere is discharged into a coagulation bath from a tube-in-orifice nozzle through an air gap (a passage where the dope runs in the air) whereupon a membrane is formed. Here, it is necessary that a nitrogen purge is repeatedly conducted for substituting the oxygen which is contained in the polymer and the solvent in order to prevent the deterioration of the spinning dope by oxygen and, after that, the nitrogen is sealed therein and heating and dissolving are conducted under such a state where oxygen is interrupted. The core solution may be a non-coagulating liquid such as liquid paraffin or isopropyl myristate or may be an aqueous coagulating liquid such as water, water and solvent or a mixture thereof with a non-solvent. It is also possible to use gas such as air.

Although the concentration of the hydrophobic polymer in the spinning dope depends upon the type of the hydrophobic polymer used, it is preferably 20 to 50% by weight, and more preferably 23 to 45% by weight. When the concentration is lower than that, it is difficult to ensure the strength of the membrane and, further, there is a high possibility that it is difficult to achieve the amount of the hydrophilic polymer intended by the present invention (i.e., the amount of the hydrophilic polymer extracted with 40% ethanol) while, when the concentration is higher than that, there is a risk that the operating ability becomes bad.

Concentration of the hydrophilic polymer in the spinning dope is preferably 1 to 15% by weight, and more preferably 1 to 10% by weight. When the concentration is lower than that, there is a high possibility that it is difficult to achieve the amount of the hydrophilic polymer intended by the present invention while, when it is higher than that, there is a high possibility that it is difficult to achieve the amount of the hydrophilic polymer extracted with 40% ethanol intended by the present invention. In addition, when the molecular weight of the hydrophilic polymer is too high, there is a problem in the solubility of the spinning dope while, when it is too low, elution from the membrane is apt to happen. Accordingly, it is preferred to be 20,000 to 1,200,000 and more preferred to be 40,000 to 1,100,000 in terms of the weight-average molecular weight.

In order to prepare the spinning dope in such a high concentration as mentioned above, a method of dissolving at high temperature is generally used. However, for suppressing the elution of the hydrophilic polymer from the hollow fiber membrane, it is necessary to prepare the spinning dope at relatively low temperature or, to be more specific, at not higher than 140° C. In order to suppress the elution of the hydrophilic polymer or, in other words, in order to suppress the outcome that the molecular weight of the hydrophilic polymer becomes low, the preparation at not higher than 135° C. is more preferred and the preparation at not higher than 130° C. is further preferred. On the other hand, when the preparation temperature is extremely low, viscosity of the spinning dope during the stirring and the dissolving becomes high and, in fact, too high pressure is applied to the spinning nozzle whereby it is not possible to extrude the spinning dope. In view of the above, the lower limit temperature of the spinning dope during preparation is preferred to be not lower than 100° C. In view of the stability of the operation, it is more preferred to be not lower than 110° C. and further preferred to be not lower than 120° C.

It was mentioned already that, for suppressing the elution of the hydrophilic polymer, it is necessary to set the temperature within an appropriate range. Similarly, for suppressing the elution of the hydrophilic polymer, the retention time from the beginning of preparing the spinning dope until the discharge thereof from the spinning nozzle is preferred to be as short as possible. It was found however that, when the spinning dope prepared within short time is used for the manufacture of the hollow fiber membrane, there is a tendency that the resulting breakage strength and breakage elongation become low and that, when the retention time becomes long, the resulting breakage strength and breakage elongation are high in a stable manner. Although the mechanism causing such a result is not clear, it is likely that the lowering in the breakage strength and the breakage elongation is resulted when the uniformity of the spinning dope is uneven or, to be more specific, undissolved fine particles, etc. are generated. When a filter is installed immediately before the spinning nozzle for a purpose of removing the undissolved fine particles and the filter diameter is made 30 μm or smaller, there is a tendency that the breakage strength and the breakage elongation become stable in desired values. Accordingly, the filter diameter is more preferred to be not more than 25 μm and further preferred to be not more than 20 μm. When the filter diameter is 10 μm or smaller, the filter pressure rises and it is not possible to prepare the membrane whereby, in view of the stability of the membrane preparation, the lower limit of the filter diameter is more preferred to be not less than 15 μm and further preferred to be not less than 20 μm.

The spinning dope is discharged from the tube-in-orifice nozzle and, after it is passed through the running passage in the air of 1 to 10 cm, it is introduced to a coagulation bath. Concentration and temperature of the coagulating liquid are 0 to 70% by weight and 0 to 30° C., respectively. More preferably, they are 20 to 70% by weight and 3 to 20° C., respectively. In the coagulating step, the spinning dope is mostly coagulated to a hollow fiber membrane in the first coagulation bath and then the hollow fiber membrane which is not completely coagulated is elongated in the second coagulation bath whereupon adjustment of the flux (water permeating property) and imparting the strength are done. In the method of the present invention, elongation is applied to the spinning dope in the coagulation bath. As a result of the elongation during this coagulating process, it is likely that, although the detailed mechanism is ambiguous, the polymer which forms the hollow fiber membrane is aligned, Young's modulus becomes high and the strength to the pressure from outside can be applied. The elongation applied here is 10 to 65% and preferably 10 to 60%. The elongation by the coagulation bath here is the ratio of the inlet roller speed of the coagulation bath to the outlet roller speed of the coagulation bath or the ratio of the inlet roller speed of the second coagulation bath to the outlet roller speed of the second coagulation bath.

When spinning of the hardly crystallizing polymer such as polysulfone or polyether sulfone is conducted using the non-coagulating inner solution, the coagulating speed is slow and, therefore, when an appropriate elongation is applied in the coagulation bath, the state of the inner surface which is the part contacting the blood is that deformation of the pore shape is not too much and alignment of the pores is high whereby a uniform and smooth state is resulted. As a result of having such a characteristic feature, adhesion of the platelets is suppressed and, further, adsorption of the blood protein is suppressed to a monomolecular layer whereby it is likely that a hollow fiber membrane can be obtained where lowering of the water permeability with an elapse of time is low even when the blood perfusion is conducted together with applying the pressure which is the characteristic feature of the present invention. There is also another effect that, as a result of the elongation, tightening of the membrane surface is suppressed, excessive hydrophilic polymer can be easily removed and the eluting amount in actual use is reduced. Moreover, as a result of conducting the elongation together with solidifying in a coagulation bath, although the detailed mechanism therefor is ambiguous, the alignment of the polymer chain is optimized in the membrane, the yield strength is significantly enhanced and the ratio of the yield strength to the yield elongation can be controlled within a preferred range.

When the hollow fiber membrane is introduced from the coagulation bath to the water washing bath, the hollow fiber membrane starts in shrinking together with the progress of the coagulation and, when the elongation is positively applied in this water washing step, the dialyzing property can be enhanced. This step disturbs the unevenness of the membrane structure formed by shrinking as the phase separation proceeds and the permeation of the solute and also removes the layer which is resistant to the dialysis whereby it is a step which gives important properties. This step is a step after the membrane structure is almost formed and, therefore, an excessive elongation results in fracture of the membrane structure, cutting of the fiber and winding of the fiber to the roller. However, application of the elongation resistant to the shrinking is important and the elongation conducted here is preferred to be applied in a divided manner according to the step numbers of the water washing baths so that the ratio of the outlet roller speed of the final water washing bath to the inlet roller speed of the first water washing bath is made within a range of 2.0 to 10%, more preferably within a range of 2.0 to 6.0%.

After the water washing baths, the hollow fiber membrane is subjected to a hydrophilizing step using a glycerol bath or the like and then dried in a drying step using a dryer or the like. Although there is no limitation at all for the hydrophilizing agent so far as it has a moisture keeping property and can be impregnated in the pores, the particularly preferred one is glycerol since it has a high result of use in the field of hemodialysis and is easily available. Concentration of the aqueous solution of glycerol necessary for keeping the pore size is 30 to 70% by weight and more preferably 40 to 60% by weight. When shrinking is applied by an excessive drying heat or when mechanical stretch is applied by means of elongation in the drying step, shrinking of the hollow fiber membrane is resulted whereupon the hydrophilizing agent floats on the surface of the hollow fiber membrane or the defect is generated in the membrane. If the hydrophilizing agent is floated on the surface of the membrane, it acts as an adhesion inhibitor among the hollow fiber membranes during the adhesion of the module thereafter, deteriorating the loosing property of the fiber whereupon there is resulted a phenomenon of reducing the assembling yield. Now, in the present invention, the drying temperature is set at 20 to 50° C. and preferably at 25 to 45° C. for suppressing the shrinking during drying of the membrane in the drying step. Further, it is necessary in the drying step that the hollow fiber membrane is substantially non-elongated (i.e., elongation of 0.5% or less) and drying is conducted by a substantially constant roller speed to conduct a sort of curing. If elongation is carried out during drying, adhesive property of the hollow fiber membrane lowers whereupon the detachment is apt to occur, the defect is resulted in the membrane, the operating ability lowers and the fiber is apt to be cut.

Thus, in the formation of the hollow fiber membrane in accordance with the present invention, the spinning dope discharged from the tube-in-orifice nozzle is elongated in a coagulation bath or in the second coagulation bath whereupon the membrane property and the pressure-resisting strength are imparted and, in the succeeding water washing step, elongation is also applied continuously. After that, a step of applying the glycerol is conducted upon necessity and, during drying, the drying is conducted substantially without elongation to cure. As such, there is conducted a membrane forming method which can be said to be an annealing spinning method. As a result, it is now possible to prepare a hollow fiber membrane where the permeating ability for the low-molecular protein is high in spite of its low water permeability, the risk of contamination of pyrogen, etc. due to a back-filtration is low and the resistance to the pressure from outside is available.

In such a view that blood compatibility, safety and efficiency-retaining ability are to be satisfied at the same time, the hollow fiber membrane of the present invention is preferred to be that its membrane thickness is 10 to 30 μm and its inner diameter is 100 to 300 μm. When the membrane thickness is too small, there may be a difficulty in ensuring the sufficient strength. The membrane thickness is more preferred to be not less than 12 μm and further preferred to be not less than 14 μm. When the membrane thickness is too big, permeating property for the substance may lower. Accordingly, the membrane thickness is more preferred to be not more than 27 μm and further preferred to be not more than 23 μm. When the inner diameter is out of the above range, flow rate of the blood during blood perfusion becomes too low or too high whereby there is a possibility of causing the lowering of the blood compatibility and the lowering of the efficiency-retaining ability because of blood component adsorption due to the interaction with the membrane surface. The inner diameter is more preferred to be 130 to 280 μm and more preferred to be 150 to 250 μm.

There has been known a technique where, after a blood purification module is assembled using the above-prepared hollow fiber membrane, γ ray or electron ray is irradiated under a predetermined condition whereupon the hydrophilic polymer is cross-linked and suppression of elution of the hydrophilic polymer is achieved. However, when this method is used, decomposition of the hydrophilic polymer (production of radical) is induced for the cross-linking whereby there is a possibility that the safety of materials or the safety in use cannot be guaranteed. Accordingly, it is preferable that the cross-linking during irradiation of γ ray or electron ray is suppressed to the minimum. To be more specific, amount of the cross-linked polymer is preferred to be not more than 5%, more preferred to be not more than 3%, and further preferred to be not more than 2% to the weight of the total membrane. Incidentally, glycerol is adhered to the hollow fiber membrane according to the present invention as a retaining agent for the membrane diameter (hydrophilizing agent) but, since glycerol has an action of inhibiting the cross-linking, amount of the cross-linked polymer to the weight of the total membrane is not more than 3%.

On the other hand, the index for the roughness of the inner surface of the hollow fiber membrane can be evaluated by observing the shape under an atomic force microscope (AFM). In the present invention, activation of the blood (formation of thrombus or residual blood) which is thought to be affected by unevenness of the area in the order of several tens μm is not evaluated but is evaluated by observing the surficial state of the unevenness (in the order of nm) of very small area which is thought to affect on the degree of easy formation of protein layer onto the inner surface of the hollow fiber membrane. Since evaluation of activation of the blood is to check how smoothly the blood (which flows in the hollow fiber membrane) flows, it is necessary to check the unevenness of the area of as wide as possible. Although it is to be the area of as wide as possible, the observation is conducted for the inner surface of the hollow fiber membrane where the inner diameter is about 200 μm whereby the area is in the order of several tens μm. In contrast thereto, the thing to be checked in the present invention is the easiness in the formation of the blood protein layer and the degree of a delicate retention of the blood protein (mostly comprising albumin where Stokes radius is 3.55 nm) on the inner surface of the hollow fiber membrane (reversible adsorption) is to be checked. Accordingly, it is appropriate to measure the range of as narrow as possible with high precision and, for example, the range measured by an AFM is appropriate to be 3 μm square. Thus, 3 μm square of the surface of the hollow fiber membrane is observed under an AFM and evaluation is done in terms of the surficial roughness (Ra) and the maximum difference between the highest and the lowest (PV value). In order to instantly form a protein adsorptive layer immediately after contacting the blood, the unevenness of such a degree that the blood protein can be delicately retained on the inner surface of the hollow fiber membrane (reversible adsorption) is necessary and Ra value and PV value are preferably not more than 15 nm and not more than 150 nm, respectively. Ra value and PV value are more preferably not more than 10 nm and not more than 140 nm, respectively. Ra value and PV value are more preferably not more than 5 nm and not more than 120 nm, respectively.

EXAMPLES

As hereunder, the effectiveness of the present invention will be illustrated by way of Examples although the present invention is not limited thereto. Incidentally, the methods for evaluations in the following Examples are as follows.

[Method for Measuring the Water Permeability of the Hollow Fiber Membrane]

A blood purification module was used and pure water of 37° C. was filled in both of the inner and the outer sides of the membrane. Pressure was applied with pure water from the inlet of the blood purification module connecting to the inside of the membrane so that the pressure difference was resulted between the inner and the outer sides of the membrane (i.e., inter-membrane pressure difference) and the amount of pure water coming out through the membrane to the outside of the membrane per minute was measured. In four different inter-membrane pressure differences, amount of the permeated water per minute was measured and plotted on the two-dimensional coordinate for the inter-membrane pressure difference and the permeated water amount and inclination of their approximate straight line was determined as a numeral. This numeral was multiplied with 60 and divided by the membrane area of the blood purification module to determine the water permeability of the hollow fiber membrane. (Hereinafter, it will be abbreviated as UFR and the unit therefor is mL/($m^2 \cdot hr \cdot mmHg$).)

[Method for Measuring the Pressure Resistance of the Hollow Fiber Membrane to the Pressure from Outside]

A blood purification module was used and pure water of 37° C. was filled in the inner side (the blood side) of the membrane. Total volume (corresponding to the filled amount of pure water) of the blood side of this blood purification module was defined as a priming volume (unit: mL). No water was filled in the dialysate side of the blood purification module but pure water was filled in the blood side only and, under such a state, pressurization of 0.1 MPa with air was applied to the dialysate side. Such a state was kept for 10 minutes and the volume of discharged pure water which was filled in the inner side due to deformation of the hollow fiber membrane by the pressure from outside was measured. When this volume was not more than one half of the priming volume, resistance to the pressure was judged to be good while, when it was more than one half, resistance to the pressure was judged to be poor.

[Test and Evaluation of the Resistance of the Blood Purification Module to the Pressure from Outside]

A blood purification module was used and pure water of 37° C. was filled in the inner side (the blood side) of the membrane. After that, no water was filled in the dialysate side of the blood purification module but pure water was filled in the blood side only and, under such a state, pressurization of 0.2 MPa with air was applied to the dialysate side. Such a state was kept for 30 minutes whereby deformation due to the pressure from outside was applied to the hollow fiber membrane and to the adhered area of the hollow fiber membrane. After that, a leakage test (an air bubble test by means of pressurization with air by dipping in water) of the blood purification module was conducted to confirm whether the leaked damage of the blood purification module happened. Also, the cross section of the blood purification module was checked under a magnifier to confirm whether the detachment happened.

[Method for Measuring the β2MG Clearance]

This was carried out according to the standard for the evaluation of the ability disclosed in the Non-Patent Document 1. In the blood purification module having the membrane area of 1.5 $m^2$ (based on the inner diameter of the hollow fiber membrane), ACD-added cow's plasma where total protein concentration was adjusted to 6.5±0.5 g/dL followed by keeping at 37° C. was circulated for 1 hour at the flow rate at the blood side of 200 mL/min. After that, ACD-added cow's plasma where human β2MG was added thereto so as to make the concentration 0.05 to 0.1 mg/L and total protein concentration was adjusted to 6.5±0.5 g/dL followed by keeping at 37° C. was flown to the blood side at the flow rate at the blood side of 200 mL/min and dialysis is carried out using 500 mL/min of a commercially available dialysate where the flow rate of the filtrate was made 15 mL/min. This clearance evaluation was conducted in a single path. Concentrations of the β2MG in the inlet and the outlet for the blood and the outlet for the dialysate were measured. The clearance was calculated according to the following formula.

$$CL(\beta 2MG)=200\times[(200\times CBi)-(185\times CBo)]/(200\times CBi)$$

In the formula, CBi was the concentration at the inlet for the blood and CBo was the concentration at the outlet for the blood.

[Method for Measuring the Backfiltration]

Measurement of the backfiltration was carried out using a blood purification module having the membrane area of 1.5 m² (based on the inner diameter of the hollow fiber membrane) and an ACD-added cow's total blood where hematocrit and total protein concentration were adjusted to 30±3% and 6.5±0.5 g/dL, respectively, followed by keeping at 37° C. ACD-added cow's plasma kept at 37° C. was flown to the blood side at the flow rate at the blood side of 200 mL/min and dialysis is carried out using 500 mL/min of a commercially available dialysate where the flow rate of the filtrate was made 8 mL/min. Here, the reason why the filtering flow rate was made as low as 8 mL/min was to confirm whether the backfiltration still took place even under the case of low water removal in the ordinary dialysis. With regard to the fact whether the backfiltration took place, the pressure (PBout) (mmHg) at the outlet side for the blood, the colloid osmotic pressure (π)(22 mmHg) and the pressure (PDin) (mmHg) at the inset side for the dialysate were measured and the case where (PBout)−(π)(22)−(PDin) was in a positive value was judged that the backfiltration did not take place while the case where the above was in a negative value was judged that the backfiltration took place.

[Method for Measuring and Calculating the Amount of Insoluble Components Contained Therein]

The hollow fiber membrane (10 g) which was the final product was dissolved in 100 mL of the solvent used for its manufacture. Insoluble components were separated from this solution by means of centrifugal separation at 1500 rpm for 10 minutes and the supernatant liquid was removed. This operation was repeated for three times, the residual insoluble components were evaporated to dryness to measure the weight and the amount of the insoluble components was calculated.

[Method for Measuring and Calculating the Amount of Hydrophilic Polymer Contained Therein]

The hollow fiber membrane was dissolved in heavy DMSO, a 1H-NMR measurement was conducted and the ratio by area of the peak derived from the hydrogen atom (say, H1) contained in the hydrophobic polymer to the peak derived from the hydrogen atom (say, H2) contained in the hydrophilic polymer was determined (This area ratio is called a1:a2.). Amount of the hydrophilic polymer contained therein was calculated by the following formula where M1 is molecular weight of the repeating unit of the hydrophobic polymer, n1 is the numbers of the above a1 contained in the repeating unit, M2 is molecular weight of the repeating unit of the hydrophilic polymer and n2 is the numbers of the above a2 contained in the repeating unit.

Amount of the hydrophilic polymer contained therein
(%)=((a2/n2)×M2×100)/((a1/n1)×M1+(a2/n2)×M2)

[Method for Extracting with a 40% Aqueous Solution of Ethanol]

An extracting test with a 40% aqueous solution of ethanol was conducted according to the following procedures. Thus, 400 mL of pure water was flushed into the inner area of the hollow fiber membrane of the blood purification module and, after that, the pure water in the blood purification module was substituted with a 40% by volume aqueous solution of ethanol. The inner area of the module case of the outside of the hollow fiber membrane was also filled and sealed with a 40% by volume aqueous solution of ethanol. After that, under the condition of 40° C., 200 mL of a 40% by volume aqueous solution of ethanol was circulated for 1 hour in the inside of the hollow fiber membrane at 150 mL/min, then the circulated 40% by volume aqueous solution of ethanol was recovered and its PVP concentration was measured. Total weight of the extracted PVP was calculated from the total volume of the extract where 200 mL was added to the priming volume (i.e. the volume of inner area of the hollow fiber membrane of the blood purification module and the volume of header areas of the outlet and inlet of the blood purification module) and the PVP concentration in the extract. Further, the extracted amount of PVP per 1 m² of the membrane area at the side contacting the solution to be treated was determined from the membrane area (based on the inner diameter) of the blood purification module.

[Method for Measuring the PVP Concentration]

Measurement of the concentration of PVP was carried out according to the method of K. Mueller (K. Mueller, Pharm. Acta. Helv., 43, 107 (1968)). Thus, citric acid and iodine solution were added to the test sample, its absorbance was measured and the concentration was determined from a calibration curve prepared from PVP of the known concentrations. In measuring the concentration, it is necessary to dilute to an extent of twice or more so as to avoid the inhibition of the coloration by ethanol. To be more specific, when the measurement of concentration was done under diluting to an extent of twice, 1.25 mL of the sample, 1.25 mL of water, 1.25 mL of 0.2 mol/L aqueous solution of citric acid and 0.5 mL of 0.006N aqueous solution of iodine were well mixed and allowed to stand for 10 minutes, then the absorbance thereof at 470 nm was measured and the concentration of PVP was calculated from the above measured value.

[Method for Measuring the C Characteristic Value of the Hollow Fiber Membrane]

A blood purification module was used and then cow's blood where hematocrit was 35% was perfused into the inner side of the hollow fiber membrane at a flow rate of 200 mL/min. At the same time, filtration was carried out at the flow rate of 20 mL/min from the outer side of the hollow fiber membrane. The water permeability (hereinafter, it may be abbreviated as MFR) in the cow's blood system was calculated from the inter-membrane pressure and the filtered liquid amount after 15 minutes starting from the perfusion and the filtration. The resulting value was called (A) while the value of MFR determined by the same operation after 120 minutes starting from the perfusion and the filtration was called (B) and the C characteristic value was calculated from the formula of 100(%)×(B)/(A).

[Method for Measuring the Clearance]

Measurement was conducted by the blood purification module having the membrane area of 1.5 m² using a diluted Kindaly solution (35-fold dilution) prepared for containing 20 ppm of vitamin $B_{12}$, 1000 ppm of urea, 180 ppm of sodium chloride, 40 ppm of monosodium phosphate (anhydride) and 480 ppm of disodium phosphate (dodecahydrate). The flow rate at the blood side was made 200±1 mL/min while the flow rate at the dialysate side was made 500±10 mL/min and the above Kindaly solution was flown at 37° C. After 1 minute from the start of the flowing, the solution at the dialysate side was sampled during three minutes while, during that period, sampling of the solution at the blood side (out) was conducted for one minute. For each of the solutions, the concentration of urea was measured by a urease-indophenol method using the Urea-Nitrogen B-Test Wako manufactured by Wako Pure Chemicals. Further, the concentration of vitamin $B_{12}$ was measured from the absorbance at 360 nm. Urea clearance (CLun) and vitamin $B_{12}$ clearance (CLvb) of the hollow fiber membrane were calculated from those measured values.

[Measurement of Inner Diameter, Outer Diameter and Membrane Thickness of the Hollow Fiber Membrane]

A sample of cross section of the hollow fiber membrane can be prepared as follows. For the measurement, it is preferred that the hollow forming material is washed and removed and, after that, the hollow fiber membrane is observed in a dry state. Although there is no limitation for the drying method, it is preferred in case the shape significantly changes by drying that the hollow forming material is washed and removed, pure water is completely substituted therefor and the shape is observed in a wet state. Inner diameter, outer diameter and membrane thickness of the hollow fiber membrane are obtained in such a manner that several appropriate numbers of the hollow fiber membranes are inserted into the pores of 3 mm diameter opened in the center of a slide glass to such an extent that the hollow fiber membranes are not dropped therethrough and cut using a razor on the upper and lower sides of the slide glass and the resulting samples of cross sections of the hollow fiber membranes are subjected to the measurement of short and long diameters of the hollow fiber membrane cross sections using a projector Nikon-V-12A. For each hollow fiber membrane cross section, short and long diameters in two ways are measured and the arithmetic mean values thereof are adopted as the inner and outer diameters of one hollow fiber membrane cross section while the membrane thickness is calculated as [(outer diameter)−(inner diameter)]/2. The same measurement is conducted for five cross sections and the mean values are adopted as the inner diameter, outer diameter and the membrane thickness.

[Method for Measuring the Yield Strength and the Yield Elongation of the Hollow Fiber Membrane]

Tensilon UTMII manufactured by Toyo Baldwin was used and the measurement was conducted where the tensile speed was 100 mm/min and the distance between the chucks was 100 mm. Measurement was conducted for five samples and the mean value thereof was used.

[Method for Measuring the Adhered Rate of Glycerol to the Hollow Fiber Membrane]

Adhered rate of glycerol to the hollow fiber membrane was measured as follows. Thus, the resulting hollow fiber membranes were made into a bundle comprising about 10,000 components and uniformly cut into about 20 cm length, a core liquid in the inner side of the hollow fiber membrane was removed by means of centrifugal liquid removal followed by drying and the weight (W) was measured. After that, the hollow fiber membrane bundle was dipped in a corresponding amount of water heated at 40° C., well washed and dried for 2 hours in a drying oven of 120° C. and the weight (P) was measured. After that, the adhered rate of glycerol (G) (in % by weight) to the hollow fiber membrane was calculated by the following formula.

$$G(\% \text{ by weight}) = (W-P)/W \times 100$$

[Method for Measuring the Shrinkage of the Hollow Fiber Membrane]

The hollow fiber membrane was uniformly cut into a length of 20.0 cm, aligned in a previously scaled plastic case which was confirmed to have no thermal shrinkage, placed in a dryer where the inside was previously heated at 80° C. without fixing the both ends of the hollow fiber membrane and continuously heated for 20 hours as it was. The hollow fiber membrane taken out therefrom was cooled at room temperature for 30 minutes and the actual length of the hollow fiber membrane was measured using the scale.

[Observation Under an AFM (Measurement of Roughness of the Inner Surface of the Hollow Fiber Membrane)]

The hollow fiber membrane to be tested where the inner surface was exposed was used as a sample. The shape was observed under an atomic force microscope SPI 3800. At that time, the observation mode was in a DFM mode, the scanner was FS-20A, the cantilever was DF-3 and the observation field was 3 μm square. The PV value is the difference between the maximum and minimum values of the unevenness of all measuring points to the standard point when the unevenness of the membrane surface was measured and the Ra value is an arithmetic mean value of unevenness of the all measuring points to the standard point.

[Leakage Rate at the Adhered Part]

The hollow fiber membrane module having the membrane area of 1.5 m² was used. Pressurization with 0.15 MPa air was applied from the blood side for 10 seconds followed by holding for 10 seconds more and the decreased pressure value (Pa) during 10 seconds thereafter was read. When the value was not more than 200 Pa, no leakage was judged to be generated while, when the value was more than 200 Pa, leakage was judged to be generated.

The leakage rate at the adhered part was determined by the following formula based on the above judgment result. Incidentally, total assembled module numbers were ten.

Leakage rate at the adhered part (%)=[(Module numbers where leakage at the adhered part was generated)/(Total assembled module numbers)]×100 (%)

The present invention 1 will now be illustrated by way of the specific examples as follows.

Example 1

PES (Sumika Excel 4800P manufactured by Sumika Chemtex) (42.5% by weight), 4.5% by weight of PVP (Kollidon K-90 manufactured by BASF), 21.2% by weight of TEG (manufactured by Mitsui Chemical) and 31.8% by weight of NMP (manufactured by Mitsubishi Chemical) were mixed, sealed by nitrogen and stirred. Then, purge with nitrogen followed by stirring was repeated for three times. Then, the temperature was raised up to 125° C. to uniformly dissolve. The resulting membrane-forming solution was subjected to a sintered filter to remove the abnormal matters. Then, this solution was discharged from a tube-in-orifice nozzle, using liquid paraffin as a core solution. The solution was passed by a spinning tube through a running part in the air of 30 mm length being shut off from the outer air, coagulated in the first coagulation bath comprising a 65 wt % aqueous solution of NMP/TEG (6/4) at 5° C., then introduced into the second coagulation bath comprising a 65 wt % aqueous solution of NMP/TEG (6/4) at 5° C. to apply the elongation of 35%, passed through water-washing baths in 15 stages with an elongation ratio of 0.3% in hot water of 65° C., then passed through a 60 wt % glycerol bath of 87° C. In the next drying using a dryer, a hot-wind drying of 60° C. was done by a relaxing-type system where no elongation was applied and no pulling was done during drying and a winding-up was conducted at the spinning speed of 60 m/min whereupon a hollow fiber membrane of 200 μm inner diameter and a membrane thickness of 17 μm was prepared.

The resulting hollow fiber membrane cheese was subjected to a stabilizing treatment for 20 hours in a dryer of 70° C. and then made into a module by a conventional method to give a blood purification module having the membrane area of 1.5 m² based on the inner diameter of the hollow fiber membrane. Result of the evaluation thereof is shown in Table 1.

In spite of the fact that the water permeability was as low as 14 mL/(m²·hr·mmHg), β2 microglobulin clearance was 18 mL/min which was high efficiency of the type II stipulated by the functional classification, resistance to the pressure was good and no backfiltration was observed. Therefore, there were obtained safe, highly efficient and useful hollow fiber membrane and blood purification module.

Example 2

A hollow fiber membrane was prepared according to the same prescription as in Example 1 except that the spinning speed was made 90 m/min and the discharged amounts of core solution and polymer solution were made 1.5-fold. Then, similarly, a hollow fiber membrane cheese was subjected to a stabilizing treatment for 20 hours in a dryer of 70° C. followed by making into a module to give a blood purification module having the membrane area of 1.5 m². Result of the evaluation thereof is shown in Table 1.

In spite of the fact that the water permeability was as low as 18 mL/(m²·hr·mmHg), β2 microglobulin clearance was 21 mL/min which was high efficiency of the type II stipulated by the functional classification, resistance to the pressure was good and no backfiltration was observed. Therefore, there were obtained safe, highly efficient and useful hollow fiber membrane and blood purification module.

Example 3

A hollow fiber membrane was prepared according to the same prescription as in Example 1 except that the components of the membrane-forming solution were made 44.5% by weight of PES (Sumika Excel 4800P manufactured by Sumika Chemtex), 5.5% by weight of PVP (Kollidon K-90 manufactured by BASF), 20% by weight of TEG (manufactured by Mitsui Chemical) and 30% by weight of NMP (manufactured by Mitsubishi Chemical), the dissolving temperature was made 130° C., the elongation in the second coagulation bath was made 55% and the elongations in the water-washing bath were made 0.35% in each bath and 5.25% in total during 15 stages. Then, similarly, a hollow fiber membrane cheese was subjected to a stabilizing treatment for 20 hours in a dryer of 70° C. followed by making into a module to give a blood purification module having the membrane area of 1.5 m². Result of the evaluation thereof is shown in Table 1.

In spite of the fact that the water permeability was as low as 18 mL/(m²·hr·mmHg), β2 microglobulin clearance was 24 mL/min which was high efficiency of the type II stipulated by the functional classification, resistance to the pressure was good and no backfiltration was observed. Therefore, there were obtained safe, highly efficient and useful hollow fiber membrane and blood purification module.

Example 4

CTA (LT105 manufactured by Daicel Chemical Industries, Ltd.) (24.3% by weight), 22.71% by weight of TEG (manufactured by Mitsui Chemical) and 52.99% by weight of NMP (manufactured by Mitsubishi Chemical) were mixed, sealed by nitrogen and stirred. Then, purge with nitrogen followed by stirring was repeated for three times. Then, the temperature was raised up to 125° C. to uniformly dissolve. The resulting membrane-forming solution was subjected to a sintered filter to remove the abnormal matters. Then, this solution was discharged from a tube-in-orifice nozzle, using liquid paraffin as a core solution. The solution was passed through a spinning tube through a running part in the air of 45 mm length being shut off from the outer air, coagulated in the first coagulation bath comprising a 30 wt % aqueous solution of NMP/TEG (7/3) at 12° C., then introduced into the second coagulation bath comprising a 30 wt % aqueous solution of NMP/TEG (7/3) at 12° C. to apply the elongation of 10%, passed through water-washing baths in 15 stages with an elongation ratio of 0.15% in hot water of 65° C., then passed through a 46 wt % glycerol bath. In the next drying using a dryer, a hot-wind drying of 65° C. was done by a relaxing-type system where no elongation was applied and no pulling was done during drying and a winding-up was conducted at the spinning speed of 80 m/min whereupon a hollow fiber membrane of 201 μm inner diameter and a membrane thickness of 15.5 μm was prepared.

The resulting hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Table 1.

In spite of the fact that the water permeability was as low as 14 mL/(m²·hr·mmHg), β2 microglobulin clearance was 14 mL/min which was high efficiency of the type II stipulated by the functional classification, resistance to the pressure was good and no backfiltration was observed. Therefore, there were obtained safe, highly efficient and useful hollow fiber membrane and blood purification module.

Comparative Example 1

A hollow fiber membrane was prepared according to the same prescription as in Example 1 except that the elongation in the second coagulation bath was made 5% and no pulling was done. Similarly, the hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Table 1.

Water permeability was as low as 13 mL/(m²·hr·mmHg) and β2 microglobulin clearance was as low as 9 mL/min which was the type I stipulated by the functional classification. Further, the resulting hollow fiber membrane was collapsed with the pressure of 0.1 MPa from outside whereby it had no sufficient resistance to the pressure.

Comparative Example 2

A hollow fiber membrane was prepared according to the same prescription as in Example 1 except that the elongation in the second coagulation bath was made 5% and no pulling was done and the elongations in the water-washing bath were made 0.1% in each bath and 1.5% in total during 15 stages. Similarly, the hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Table 1.

Water permeability was as low as 12 mL/(m²·hr·mmHg) and β2 microglobulin clearance was as low as 6 mL/min which was the type I stipulated by the functional classification. Further, the resulting hollow fiber membrane was collapsed with the pressure of 0.1 MPa from outside whereby it had no sufficient resistance to the pressure.

Comparative Example 3

A hollow fiber membrane was prepared according to the same prescription as in Example 1 except that, in drying with a dryer after passing through a glycerol bath, the drying was conducted with hot wind of 60° C. together with applying the elongations of 0.1% in each stage and 1.0% in total by ten stages so as to stabilize the running. Similarly, the hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Table 1.

Water permeability was as low as 14 mL/(m²·hr·mmHg) and β2 microglobulin clearance was as low as 9 mL/min which was the type I stipulated by the functional classification. When the pressure of 0.2 MPa was applied from outside, leakage was generated in ten blood purification modules and the resulting hollow fiber membrane and blood purification module were with insufficient adhering strength and low safety where detachment was generated on the terminal of the blood purification module.

Comparative Example 4

PES (Sumika Excel 4800P manufactured by Sumika Chemtex) (26.0% by weight), 5.5% by weight of PVP (Kollidon K-90 manufactured by BASF), 27.4% by weight of TEG (manufactured by Mitsui Chemical) and 41.1% by weight of NMP (manufactured by Mitsubishi Chemical) were mixed, sealed by nitrogen and stirred. Then, purge with nitrogen followed by stirring was repeated for three times. Then, the temperature was raised up to 125° C. to uniformly dissolve. The resulting membrane-forming solution was subjected to a sintered filter to remove the abnormal matters. Then, this solution was discharged from a tube-in-orifice nozzle, using liquid paraffin was used as a core solution. The solution by a spinning tube through a running part in the air of 30 mm length being shut off from the outer air, coagulated in a 30 wt % aqueous solution of NMP/TEG (6/4) at 5° C., then introduced into the second coagulation bath comprising a 30 wt % aqueous solution of NMP/TEG (6/4) at 5° C. to apply the elongation of 5% only, passed through water-washing baths in 15 stages with an elongation ratio of 0.1% (i.e. without elongation) in hot water of 65° C., then passed through a 65 wt % glycerol bath of 87° C. In the next drying using a dryer, a hot-wind drying of 60° C. was done by a relaxing-type system where no elongation was applied and no pulling was done during drying and a winding-up was conducted at the spinning speed of 60 m/min whereupon a hollow fiber membrane of 200 μm inner diameter and a membrane thickness of 16 μm was prepared.

The resulting hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Table 1.

In spite of its high water permeability of 62 mL/(m²·hr·mmHg), β2 microglobulin clearance was 15 mL/min and, although it was the type II stipulated by the functional classification, the value was not appreciable. Further, it was collapsed with the pressure of 0.1 MPa from outside whereby the resistance to the pressure is poor and the backfiltration also happened. Thus, it was not possible to prepare the aimed hollow fiber membrane and blood purification module being safe, highly efficient and useful.

TABLE 1

| | Example 1 | Example 2 | Example 3 | Example 4 | Comparative Example 1 | Comparative Example 2 | Comparative Example 3 | Comparative Example 4 |
|---|---|---|---|---|---|---|---|---|
| Polymer | PES | PES | PES | CTA | PES | PES | PES | PES |
| Spinning speed (m/min) | 60 | 90 | 60 | 80 | 60 | 60 | 60 | 60 |
| Dissolving temperature (° C.) | 125 | 130 | 125 | 170 | 125 | 125 | 125 | 80 |
| Polymer concentration (%) | 42.5 | 42.5 | 44.5 | 24.3 | 42.5 | 42.5 | 42.5 | 26.0 |
| PVP concentration (%) | 4.5 | 4.5 | 5.5 | 0% | 4.5 | 4.5 | 4.5 | 5.5 |
| Coagulation bath composition × temperature | 65% × 5° C. | 65% × 5° C. | 65% × 5° C. | 35% × 12° C. | 65% × 5° C. | 65% × 5° C. | 65% × 5° C. | 30% × 5° C. |
| Elongation in the second coagulation bath | 35% | 35% | 55% | 10% | 5% | 5% | 35% | 5% |
| Elongation in the water-washing bath | 4.5% | 4.5% | 5.25% | 2.25% | 4.5% | 1.5% | 1.5% | 1.5% |
| Glycerol concentration in the glycerol bath | 60% | 60% | 60% | 46% | 60% | 60% | 60% | 65% |
| Elongation in the dryer | 0% Relaxing-type | 0% Relaxing-type | 0% Relaxing-type | 0% Relaxing-type | 0% Relaxing-type | 0% Relaxing-type | 1.5% Elongation-type | 0% Relaxing-type |
| Water permeability (mL/(m² · hr · mmHg)) | 14 | 18 | 18 | 14 | 13 | 12 | 14 | 62 |
| β2MG clearance (mL/min) | 18 | 21 | 24 | 14 | 9 | 6 | 9 | 15 |
| Pressure resistance (0.1 MPa) Discharged volume | No collapse 7 ml | No collapse 7 ml | No collapse 4 ml | No collapse 26 ml | Collapse happened 56 ml | Collapse happened 61 ml | No collapse 9 ml | Collapse happened 69 ml |

TABLE 1-continued

|  | Example 1 | Example 2 | Example 3 | Example 4 | Comparative Example 1 | Comparative Example 2 | Comparative Example 3 | Comparative Example 4 |
| --- | --- | --- | --- | --- | --- | --- | --- | --- |
| Pressure resistance (0.2 MPa) Presence or absence of leakage/detachment confirmation | No leakage | No leakage | No leakage | No leakage | No leakage | No leakage | Detachment generated (two out of ten modules) | No leakage |
| Backfiltration | Positive pressure No back-filtration | Positive pressure No back-filtration | Positive pressure No back-filtration | Positive pressure No back-filtration | Positive pressure No back-filtration | Positive pressure No back-filtration | Positive pressure No back-filtration | Negative pressure Back-filtration took place |

The present invention 2 will now be illustrated by way of the specific examples as follows.

Example 5

PES (Sumika Excel 4800P manufactured by Sumika Chemtex) (42.5% by weight), 4.5% by weight of PVP (Kollidon K-90 manufactured by BASF), 21.2% by weight of TEG (manufactured by Mitsui Chemical) and 31.8% by weight of NMP (manufactured by Mitsubishi Chemical) were mixed, sealed by nitrogen and stirred. Then, purge with nitrogen followed by stirring was repeated for three times. Then, the temperature was raised up to 125° C. to uniformly dissolve. The resulting membrane-forming solution was subjected to a sintered filter to remove the abnormal matters. Then, this solution was discharged from a tube-in-orifice nozzle, using liquid paraffin as a core solution. The solution was passed by a spinning tube through a running part in the air of 25 mm length being shut off from the outer air, coagulated in the first coagulation bath comprising a 65 wt % aqueous solution of NMP/TEG (6/4) at 5° C., then introduced into the second coagulation bath comprising a 65 wt % aqueous solution of NMP/TEG (6/4) at 5° C. to apply the elongation of 35%, passed through water-washing baths in 15 stages with an elongation ratio of 0.3% in hot water of 65° C., then passed through a 60 wt % glycerol bath of 87° C. In the next drying using a dryer, a hot-wind drying of 60° C. was done by a relaxing-type system where no elongation was applied and no pulling was done during drying and a winding-up to a bobbin in cross-wind was conducted at the spinning speed of 60 m/min whereupon a hollow fiber membrane of 198 μm inner diameter and a membrane thickness of 17 μm was prepared.

The resulting hollow fiber membrane cheese was subjected to a stabilizing treatment for 20 hours in a dryer of 70° C. and then made into a module by a conventional method to give a blood purification module having the membrane area of 1.5 m² based on the inner diameter of the hollow fiber membrane. Result of the evaluation thereof is shown in Tables 2 and 3.

Example 6

A hollow fiber membrane was prepared according to the same prescription as in Example 1 except that the components of the membrane-forming solution were made 41.5% by weight of PES (Sumika Excel 4800P manufactured by Sumika Chemtex), 3.5% by weight of PVP (Kollidon K-90 manufactured by BASF), 22% by weight of TEG (manufactured by Mitsui Chemical) and 33% by weight of NMP (manufactured by Mitsubishi Chemical), the dissolving temperature was made 120° C., the elongation in the second coagulation bath was made 30% and the elongation in the water-washing bath was made 0.25% in each bath and 3.75% in total during 15 stages. Then, similarly, a hollow fiber membrane cheese was subjected to a stabilizing treatment for 20 hours in a dryer of 70° C. followed by making into a module to give a blood purification module having the membrane area of 1.5 m². Result of the evaluation thereof is shown in Tables 2 and 3.

Example 7

A hollow fiber membrane was prepared according to the same prescription as in Example 1 except that the components of the membrane-forming solution were made 44.5% by weight of PES (Sumika Excel 4800P manufactured by Sumika Chemtex), 5.5% by weight of PVP (Kollidon K-90 manufactured by BASF), 20% by weight of TEG (manufactured by Mitsui Chemical) and 30% by weight of NMP (manufactured by Mitsubishi Chemical), the dissolving temperature was made 130° C., the elongation in the second coagulation bath was made 55% and the elongations in the water-washing bath were made 0.35% in each bath and 5.25% in total during 15 stages. Then, similarly, a hollow fiber membrane cheese was subjected to a stabilizing treatment for 20 hours in a dryer of 70° C. followed by making into a module to give a blood purification module having the membrane area of 1.5 m². Result of the evaluation thereof is shown in Tables 2 and 3.

Example 8

A hollow fiber membrane was prepared according to the same prescription as in Example 5 and a blood purification module was prepared similarly except that the discharged amount of the membrane-forming solution was increased whereby a hollow fiber membrane of 196 μm inner diameter and 28 μm membrane thickness was prepared.

Comparative Example 5

A hollow fiber membrane of 198 μm inner diameter and a membrane thickness of 16 μm was prepared according to the same prescription as in Example 5 except that the elongation in the second coagulation bath was made 5% and no pulling was done. Similarly, the hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Tables 2 and 3.

Water permeability was as low as 13 mL/(m²·hr·mmHg) and β2 microglobulin clearance was as low as 9 mL/min which was the type I stipulated by the functional classification. Further, the resulting hollow fiber membrane was collapsed with the pressure of 0.1 MPa from outside whereby it had no sufficient resistance to the pressure.

Comparative Example 6

A hollow fiber membrane of 201 μm inner diameter and a membrane thickness of 15 μm was prepared according to the same prescription as in Example 5 except that the elongation in the second coagulation bath was made 5% and no pulling was done and the elongations in the water-washing bath were made 0.1% in each bath and 1.5% in total during 15 stages. Similarly, the hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Tables 2 and 3.

Water permeability was as low as 12 mL/(m²·hr·mmHg) and β2 microglobulin clearance was as low as 6 mL/min which was the type I stipulated by the functional classification. Further, the resulting hollow fiber membrane was collapsed with the pressure of 0.1 MPa from outside whereby it had no sufficient resistance to the pressure.

Comparative Example 7

A hollow fiber membrane of 200 μm inner diameter and a membrane thickness of 17 μm was prepared according to the same prescription as in Comparative Example 6 except that, the elongations in the water-washing bath were made 0.1% in each bath and 1.5% in total during 15 stages, and in drying with a dryer after passing through a glycerol bath, the drying was conducted with hot wind of 60° C. together with applying the elongations of 0.15% in each stage and 1.5% in total by ten stages so as to stabilize the running. Similarly, the hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Tables 2 and 3.

Water permeability was as low as 14 mL/(m²·hr·mmHg) and β2 microglobulin clearance was as low as 9 mL/min which was the type I stipulated by the functional classification. When the pressure of 0.2 MPa was applied from outside, leakage was generated in two out of ten blood purification modules and the resulting hollow fiber membrane and blood purification module were with insufficient adhering strength and low safety where detachment was generated on the terminal of the blood purification module.

Comparative Example 8

PES (Sumika Excel 4800P manufactured by Sumika Chemtex) (26.0% by weight), 5.5% by weight of PVP (Kollidon K-90 manufactured by BASF), 27.4% by weight of TEG (manufactured by Mitsui Chemical) and 41.1% by weight of NMP (manufactured by Mitsubishi Chemical) were mixed, sealed by nitrogen and stirred. Then, purge with nitrogen followed by stirring was repeated for three times. Then, the temperature was raised up to 80° C. to uniformly dissolve. The resulting membrane-forming solution was subjected to a sintered filter to remove the abnormal matters. Then, this solution was discharged from a tube-in-orifice nozzle, using liquid paraffin as a core solution. The solution was passed by a spinning tube through a running part in the air of 30 mm length being shut off from the outer air, coagulated in a 30 wt % aqueous solution of NMP/TEG (6/4) at 5° C., then introduced into the second coagulation bath comprising a 30 wt % aqueous solution of NMP/TEG (6/4) at 5° C. to apply the elongation of 5% only, passed through water-washing baths in 15 stages with an elongation ratio of 0.1% (i.e. without elongation) in hot water of 65° C., then passed through a 65 wt % glycerol bath of 87° C. In the next drying using a dryer, a hot-wind drying of 60° C. was done by a relaxing-type system where no elongation was applied and no pulling was done during drying and a winding-up was conducted at the spinning speed of 60 m/min whereupon a hollow fiber membrane of 199 μm inner diameter and a membrane thickness of 15 μm was prepared.

The resulting hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Tables 2 and 3.

In spite of its high water permeability of 62 mL/(m²·hr·mmHg), β2 microglobulin clearance was 15 mL/min and, although it was the type II stipulated by the functional classification, the value was not appreciable. Further, it was collapsed with the pressure of 0.1 MPa from outside whereby the resistance to the pressure is poor and the backfiltration was also happened. Thus, it was not possible to prepare the aimed hollow fiber membrane and blood purification module being safe, highly efficient and useful.

TABLE 2

|  | Example 5 | Example 6 | Example 7 | Example 8 | Comparative Example 5 | Comparative Example 6 | Comparative Example 7 | Comparative Example 8 |
| --- | --- | --- | --- | --- | --- | --- | --- | --- |
| Polymer | PES | PES | PES | PES | PES | PES | PES | PES |
| Spinning speed (m/min) | 60 | 60 | 60 | 60 | 60 | 60 | 60 | 60 |
| Dissolving temperature (° C.) | 125 | 120 | 130 | 125 | 125 | 125 | 125 | 80 |
| Polymer concentration (%) | 42.5 | 41.5 | 44.5 | 42.5 | 42.5 | 42.5 | 42.5 | 26.0 |
| PVP concentration (%) | 4.5 | 3.5 | 5.5 | 4.5 | 4.5 | 4.5 | 4.5 | 5.5 |
| Coagulation bath composition × temperature | 65% × 5° C | 65% × 5° C. | 65% × 5° C. | 65% × 5° C. | 65% × 5° C. | 65% × 5° C. | 65% × 5° C. | 30% × 5° C. |
| Elongation in the second coagulation bath (%) | 35 | 30 | 55 | 35 | 5 | 5 | 35 | 5 |
| Elongation in the water-washing bath (%) | 4.5 | 3.75 | 5.25 | 4.5 | 4.5 | 1.5 | 1.5 | 1.5 |
| Glycerol concentration in the glycerol bath (%) | 60 | 60 | 60 | 60 | 60 | 60 | 60 | 65 |
| Elongation in the dryer (%) | 0 Relaxing-type | 0 Relaxing-type | 0 Relaxing-type | 0 Relaxing-type | 0 Relaxing-type | 0 Relaxing-type | 1.5 Elongation-type | 0 Relaxing-type |

TABLE 3

|  | Example 5 | Example 6 | Example 7 | Example 8 | Comparative Example 5 | Comparative Example 6 | Comparative Example 7 | Comparative Example 8 |
|---|---|---|---|---|---|---|---|---|
| Water permeability (ml/(m² · hr · mmHg)) | 14 | 18 | 18 | 11 | 13 | 12 | 14 | 62 |
| Urea clearance (ml/(min · 1 m²)) | 169 | 176 | 170 | 160 | 168 | 166 | 170 | 179 |
| Urea clearance (after heating treatment) | 167 | 173 | 169 | 158 | 152 | 147 | 161 | 164 |
| β2MG clearance (ml/(min · 1.5 m²))) | 18 | 21 | 24 | 12 | 9 | 6 | 9 | 15 |
| PVP amount (% by weight) | 17 | 15 | 19 | 16 | 17 | 17 | 17 | 23 |
| PVP eluting amount (mg/m²) | 4.5 | 3.3 | 4.7 | 4.9 | 5.5 | 7.5 | 5.1 | 12.5 |
| Yield strength (g/filament) | 43.5 | 41.1 | 44.6 | 63.7 | 34.4 | 33.5 | 34.1 | 29.7 |
| Yield elongation (%/filament) | 5.1 | 4.7 | 5.3 | 6.9 | 5.5 | 5.3 | 5.8 | 3.3 |
| Breakage strength (g/filament) | 52.8 | 50.4 | 57.7 | 72.4 | 43.5 | 41.6 | 42.9 | 37.2 |
| Breakage elongation (%/filament) | 82.6 | 72.7 | 93.7 | 103.0 | 62.1 | 58.4 | 63.3 | 41.4 |
| Length after heating treatment (cm) | 19.5 | 19.2 | 19.8 | 19.6 | 17.8 | 17.5 | 18.6 | 17.2 |
| Surficial roughness Ra (nm) | 2.5 | 3.2 | 2.2 | 3.1 | 4.6 | 4.7 | 3.5 | 3.7 |

The present invention 3 will now be illustrated by way of the specific examples as follows.

Example 9

PES (Sumika Excel 4800P manufactured by Sumika Chemtex) (42.5% by weight), 4.5% by weight of PVP (Kollidon K-90 manufactured by BASF), 21.2% by weight of TEG (manufactured by Mitsui Chemical) and 31.8% by weight of NMP (manufactured by Mitsubishi Chemical) were mixed, sealed by nitrogen and stirred. Then, purge with nitrogen followed by stirring was repeated for three times. Then, the temperature was raised up to 125° C. to uniformly dissolve. The resulting membrane-forming solution was subjected to a sintered filter to remove the abnormal matters. Then, this solution was discharged from a tube-in-orifice nozzle, using liquid paraffin as a core solution. The solution was passed by a spinning tube through a running part in the air of 30 mm length being shut off from the outer air, coagulated in the first coagulation bath comprising a 65 wt % aqueous solution of NMP/TEG (6/4) at 5° C., then introduced into the second coagulation bath comprising a 65 wt % aqueous solution of NMP/TEG (6/4) at 5° C. to apply the elongation of 35%, passed through water-washing baths in 15 stages with an elongation ratio of 0.3% (total of the elongation: 4.5%) in hot water of 65° C., then passed through a 60 wt % glycerol bath of 87° C. In the next drying using a dryer, a hot-wind drying of 40° C. was done by a relaxing-type system where no elongation was applied and no pulling was done during drying and a winding-up was conducted at the spinning speed of 60 m/min whereupon a hollow fiber membrane of 200 μm inner diameter and a membrane thickness of 17 μm was prepared.

The resulting hollow fiber membrane cheese was subjected to a stabilizing treatment for 20 hours in a dryer of 70° C. and then made into a module by a conventional method to give a blood purification module having the membrane area of 1.5 m² based on the inner diameter of the hollow fiber membrane. Result of the evaluation thereof is shown in Table 4.

Example 10

A hollow fiber membrane was prepared according to the same prescription as in Example 9 except that the spinning speed was made 90 m/min and the discharged amounts of core solution and polymer solution were made 1.5-fold. Then, similarly, a hollow fiber membrane cheese was subjected to a stabilizing treatment for 20 hours in a dryer of 70° C. followed by making into a module to give a blood purification module having the membrane area of 1.5 m². Result of the evaluation thereof is shown in Table 4.

Example 11

A hollow fiber membrane was prepared according to the same prescription as in Example 9 except that the components of the membrane-forming solution were made 44.5% by weight of PES (Sumika Excel 4800P manufactured by Sumika Chemtex), 5.5% by weight of PVP (Kollidon K-90 manufactured by BASF), 20% by weight of TEG (manufactured by Mitsui Chemical) and 30% by weight of NMP (manufactured by Mitsubishi Chemical), the dissolving temperature was made 130° C., the elongation in the second coagulation bath was made 55% and the elongations in the water-washing bath were made 0.35% in each bath and 5.25% in total during 15 stages. Then, similarly, a hollow fiber membrane cheese was subjected to a stabilizing treatment for 20 hours in a dryer of 70° C. followed by making into a module to give a blood purification module having the membrane area of 1.5 m². Result of the evaluation thereof is shown in Table 4.

Example 12

A hollow fiber membrane was prepared according to the same prescription as in Example 9 except that component of the membrane-forming solution was made 4.7% by weight of PVP (Kollidon K-90 manufactured by BASF) and passed through a 56 wt % glycerol bath of 87° C. Similarly, the hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Table 4.

Example 13

A hollow fiber membrane was prepared according to the same prescription as in Example 9 except that the elongation in the second coagulation bath was made 15%. Similarly, the hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Table 4.

Example 14

A hollow fiber membrane was prepared according to the same prescription as in Example 9 except that the elongations in the water-washing bath were made 0.17% in each bath and 2.55% in total during 15 stages. Similarly, the hollow fiber membrane cheese was subjected to a stabilizing treatment for 20 hours in a dryer of 70° C. followed by making into a module to give a blood purification module having the membrane area of 1.5 m². Result of the evaluation thereof is shown in Table 4.

Example 15

A hollow fiber membrane was prepared according to the same prescription as in Example 9 except that, in drying with a dryer, a hot-wind drying of 30° C. was done by a relaxing-type system without pulling. Similarly, the hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Table 4.

Comparative Example 9

A hollow fiber membrane was prepared according to the same prescription as in Example 9 except that the elongation in the second coagulation bath was made 5%. Similarly, the hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Table 5.

Comparative Example 10

A hollow fiber membrane was prepared according to the same prescription as in Example 9 except that the elongation in the second coagulation bath was made 5% and the elongations in the water-washing bath were made 0.1% in each bath and 1.5% in total during 15 stages. The resulting hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Table 5.

Comparative Example 11

A hollow fiber membrane was prepared according to the same prescription as in Example 9 except that, in drying with a dryer, the elongations of 0.1% in each stage and 1.5% in total by 15 stages was applied so as to stabilize the running. Similarly, the hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Table 5.

Comparative Example 4

A hollow fiber membrane was prepared according to the same prescription as in Example 9 except that, in drying with a dryer, the drying was conducted with hot wind of 60° C. Similarly, the hollow fiber membrane cheese was subjected to a stabilizing treatment for 20 hours in a dryer of 70° C. and then made into a module by a conventional method to give a blood purification module having the membrane area of 1.5 m². Result of the evaluation thereof is shown in Table 5.

TABLE 4

| | Example 9 | Example 10 | Example 11 | Example 12 | Example 13 | Example 14 | Example 15 |
|---|---|---|---|---|---|---|---|
| Polymer | PES | PES | PES | PES | PES | PES | PES |
| Spinning speed | 60 m/min | 90 m/min | 60 m/min | 60 m/min | 60 m/min | 60 m/min | 60 m/min |
| Dissolving temperature (° C.) | 125 | 130 | 125 | 125 | 125 | 125 | 125 |
| Polymer concentration (%) | 42.5 | 42.5 | 44.5 | 42.5 | 42.5 | 42.5 | 42.5 |
| PVP concentration (%) | 4.5 | 4.5 | 5.5 | 4.7 | 4.5 | 4.5 | 4.5 |
| Coagulation bath composition × temperature | 65% × 5° C. | 65% × 5° C. | 65% × 5° C. | 65% × 5° C. | 65% × 5° C. | 65% × 5° C. | 65% × 5° C. |
| Elongation in the second coagulation bath | 35% | 35% | 55% | 35% | 15% | 35% | 35% |
| Elongation in the water-washing bath | 4.5% | 4.5% | 5.25% | 4.5% | 4.5% | 2.55% | 4.5% |
| Glycerol concentration in the glycerol bath | 60% | 60% | 60% | 56% | 60% | 60% | 60% |
| Elongation in the dryer | 0% Relaxing-type | 0% Relaxing-type | 0% Relaxing-type | 0% Relaxing-type | 0% Relaxing-type | 0% Relaxing-type | 0% Relaxing-type |
| Dryer temperature | 40° C. | 40° C. | 40° C. | 40° C. | 40° C. | 40° C. | 30° C. |
| Water permeability (mL/(m² · hr · mmHg)) | 14 | 18 | 18 | 13 | 12 | 13 | 13 |
| Yield strength | 40 g | 40 g | 45 g | 40 g | 35 g | 38 g | 38 g |
| Retaining ratio of the water permeability after the repeated loading of pressure from outside | 90% | 90% | 90% | 90% | 85% | 85% | 85% |
| Pressure resistance (0.1 MPa) | No collapse | No collapse | No collapse | No collapse | No collapse | No collapse | No collapse |
| Discharged volume | 7 ml | 7 ml | 4 ml | 4 ml | 10 ml | 8 ml | 8 ml |
| Pressure resistance (0.2 MPa) Presence or absence of leakage/detachment confirmation | No leakage | No leakage | No leakage | No leakage | No leakage | No leakage | No leakage |
| Leakage rate at the adhered part | 0% | 0% | 0% | 0% | 0% | 0% | 0% |

TABLE 5

|  | Comparative Example 9 | Comparative Example 10 | Comparative Example 11 | Comparative Example 12 |
|---|---|---|---|---|
| Polymer | PES | PES | PES | PES |
| Spinning speed | 60 m/min | 60 m/min | 60 m/min | 60 m/min |
| Dissolving temperature (° C.) | 125 | 125 | 125 | 125 |
| Polymer concentration (%) | 42.5 | 42.5 | 42.5 | 42.5 |
| PVP concentration (%) | 4.5 | 4.5 | 4.5 | 4.5 |
| Coagulation bath composition × temperature | 65% × 5° C. | 65% × 5° C. | 65% × 5° C. | 65% × 5° C. |
| Elongation in the second coagulation bath | 5% | 5% | 35% | 35% |
| Elongation in the water-washing bath | 4.5% | 1.5% | 4.5% | 4.5% |
| Glycerol concentration in the glycerol bath | 60% | 60% | 60% | 60% |
| Elongation in the dryer | 0% Relaxing-type | 0% Relaxing-type | 1.5% Elongation-type | 0% Relaxing-type |
| Dryer temperature | 40° C. | 40° C. | 40° C. | 60° C. |
| Water permeability (mL/(m$^2$·hr·mmHg)) | 13 | 12 | 14 | 12 |
| Yield strength | 30 g | 30 g | 40 g | 40 g |
| Retaining ratio of the water permeability after the repeated loading of pressure from outside | 70% | 70% | 90% | 90% |
| Pressure resistance (0.1 MPa) Discharged volume | Collapse happened 56 ml | Collapse happened 61 ml | No collapse 9 ml | No collapse 9 ml |
| Pressure resistance (0.2 MPa) Presence or absence of leakage/detachment confirmation | No leakage | No leakage | Leakage happened (two out of ten modules) Detachment confirmed | No leakage |
| Leakage rate at the adhered part | 0% | 0% | 0% | 20% |

It is apparent from Tables 4 and 5 that the hollow fiber membranes of Examples 9 to 15 are with safety and high productivity where the resistance to the pressure from outside is good and no leakage was noted at the adhered part while the high retentive rate for water permeability is still available. On the contrary, the hollow fiber membranes of Comparative Examples 9 to 12 have problems in any of the terms of retentive rate for water permeability, resistance to pressure from outside and leakage at the adhered part.

INDUSTRIAL APPLICABILITY

It has been shown that, in the hollow fiber membrane and blood purification module of the present invention, although the water permeability at 37° C. was as low as 1 to 20 mL/(m$^2$·hr·mmHg), the β2 microglobulin clearance in a blood purification module having the membrane area of 1.5 m$^2$ was with a dialysis property of as high as not less than 10 mL/min (the high efficiency of type II or higher according to the functional classification stipulated by the Japanese Society for Dialysis Therapy). It has been further shown that, due to the low water permeability and the high strength thereof, resistance to the pressure was available even when the pressure of 0.1 MPa was applied from the dialysate side and, even when the pressure of 0.2 MPa was applied for 4 hours, neither detachment nor leakage of the hollow fiber membrane happened. It has been therefore shown that a risk where the dialysate invaded into a patient during the dialysis therapy or the so-called risk of backfiltration was not substantially resulted. In the hollow fiber membrane of the present invention, the hydrophilic polymer therein was hardly eluted out, its retentive property of the efficiency when used in contacting the blood was excellent, its assembling property into a module was excellent and it was suitable for a long-term preservation. Thus, it is the hollow fiber membrane which satisfies all of blood compatibility, safety, efficiency-retaining ability, economy and long-term preservation. As a result, it has advantages that, in the handling in the actual clinical fields, a risk of leakage of blood is small and, even when shock is applied thereto, the stable efficiency still can be expected. Consequently, the present invention greatly contributes to the industry concerned.

The invention claimed is:

1. A hollow fiber membrane, excellent in safety, which is characterized in that, although its water permeability at 37° C. is as low as 1 to 20 mL/(m$^2$·hr·mmHg), it has such a high dialysis performance that the clearance of β2 microglobulin in a blood purification module having 1.5 m$^2$ membrane area based on the inner diameter of the hollow fiber membrane is not less than 10 mL/min, it has such a stability that the pressure resistance from outside of the hollow fiber membrane is not less than 0.1 MPa and it substantially causes no backfiltration,
   wherein the membrane thickness of the hollow fiber membrane is 10 to 30 μm, and the membrane structure of the hollow fiber membrane is in a substantially uniform structure.

2. The hollow fiber membrane according to claim 1, wherein the hollow fiber membrane is formed from a hydrophobic polymer or from a hydrophobic polymer and a hydrophilic polymer.

3. A blood purification module, characterized in that, a plurality of the hollow fiber membranes according to claim 2 are bundled and received in a case, the end of said membrane and the end of the case are fixed with each other using an adhesive resin and then both ends are cut to open the hollow area.

4. A blood purification module, characterized in that, a plurality of the hollow fiber membranes according to claim 1 are bundled and received in a case, the end of said membrane and the end of the case are fixed with each other using an adhesive resin and then both ends are cut to open the hollow area.

5. The blood purification module excellent in safety according to claim 4, wherein neither detachment nor leakage of the hollow fiber membrane from adhesive resin happens even when the pressure of 0.2 MPa is applied from outside of the hollow fiber membrane.

* * * * *